United States Patent [19]

Yoshida et al.

[11] Patent Number: 5,426,709
[45] Date of Patent: Jun. 20, 1995

[54] METHOD OF AND APPARATUS FOR BONE MEASUREMENT

[75] Inventors: Makoto Yoshida, Kobe; Yasuki Hanaoka; Kenji Morimoto, both of Ibaraki; Hitoshi Nakamura; Takayuki Ishizaki, both of Iwakuni, all of Japan

[73] Assignee: Teijin Limited, Osaka, Japan

[21] Appl. No.: 70,796

[22] Filed: Jun. 3, 1993

[30] Foreign Application Priority Data

Jun. 4, 1992 [JP] Japan .................................. 4-144235
Aug. 13, 1992 [JP] Japan .................................. 4-216109

[51] Int. Cl.⁶ .............................................. G06K 9/00
[52] U.S. Cl. .................................... 382/132; 348/243
[58] Field of Search ..................... 382/6; 364/413.13; 250/390.02; 128/659, 653.1; 378/53, 54; 348/243

[56] References Cited

U.S. PATENT DOCUMENTS

| | | | |
|---|---|---|---|
| 4,721,112 | 1/1988 | Hirano et al. | 128/659 |
| 4,870,694 | 9/1989 | Takeo | 382/6 |
| 4,903,203 | 2/1990 | Yamashita et al. | 364/413.15 |
| 4,951,201 | 8/1990 | Takeo et al. | 382/6 |
| 4,995,093 | 2/1991 | Funahashi et al. | 382/6 |
| 5,216,511 | 6/1993 | Tani | 348/243 |

FOREIGN PATENT DOCUMENTS

| | | |
|---|---|---|
| 0411155 | 2/1991 | European Pat. Off. . |
| WO9009761 | 9/1990 | Japan ................... A61B 10/00 |
| 349 | 1/1991 | Japan . |
| 3272753 | 12/1991 | Japan . |
| 4174650 | 6/1992 | Japan . |

Primary Examiner—Leo H. Boudreau
Attorney, Agent, or Firm—Sughrue, Mion, Zinn, Macpeak & Seas

[57] ABSTRACT

A bone data measurement method and apparatus, using an X-ray picture film having a picture of the sample bone and a picture of the standard matter having gradational steps therein, e.g., an aluminum step wedge, in which a cursory reading of the pictures of the X-ray film is implemented through detection of a quantity level of light that transmits through the X-ray picture film, determining the maximum quantity level ICmax of the transmitting light that transmits through the examined region of the picture of the sample bone, minutely reading the picture of the standard matter so as to find a thickness portion $R_1$ of the standard matter, in which thickness portion a quantity level of transmitting light that transmits through the thickness portion is larger than and close to ICmax, and adjustably changing illuminating light for illuminating the X-ray picture film so that the quantity level $I_{R1}$ of the transmitting light transmitting through the thickness portion $R_1$ of the standard matter is within a predetermined quantity range of light. A temperature compensation for an output from the transmitting light detecting unit, i.e., a CCD image sensor is carried out by utilizing a light shielded output from the CCD image sensor.

14 Claims, 16 Drawing Sheets

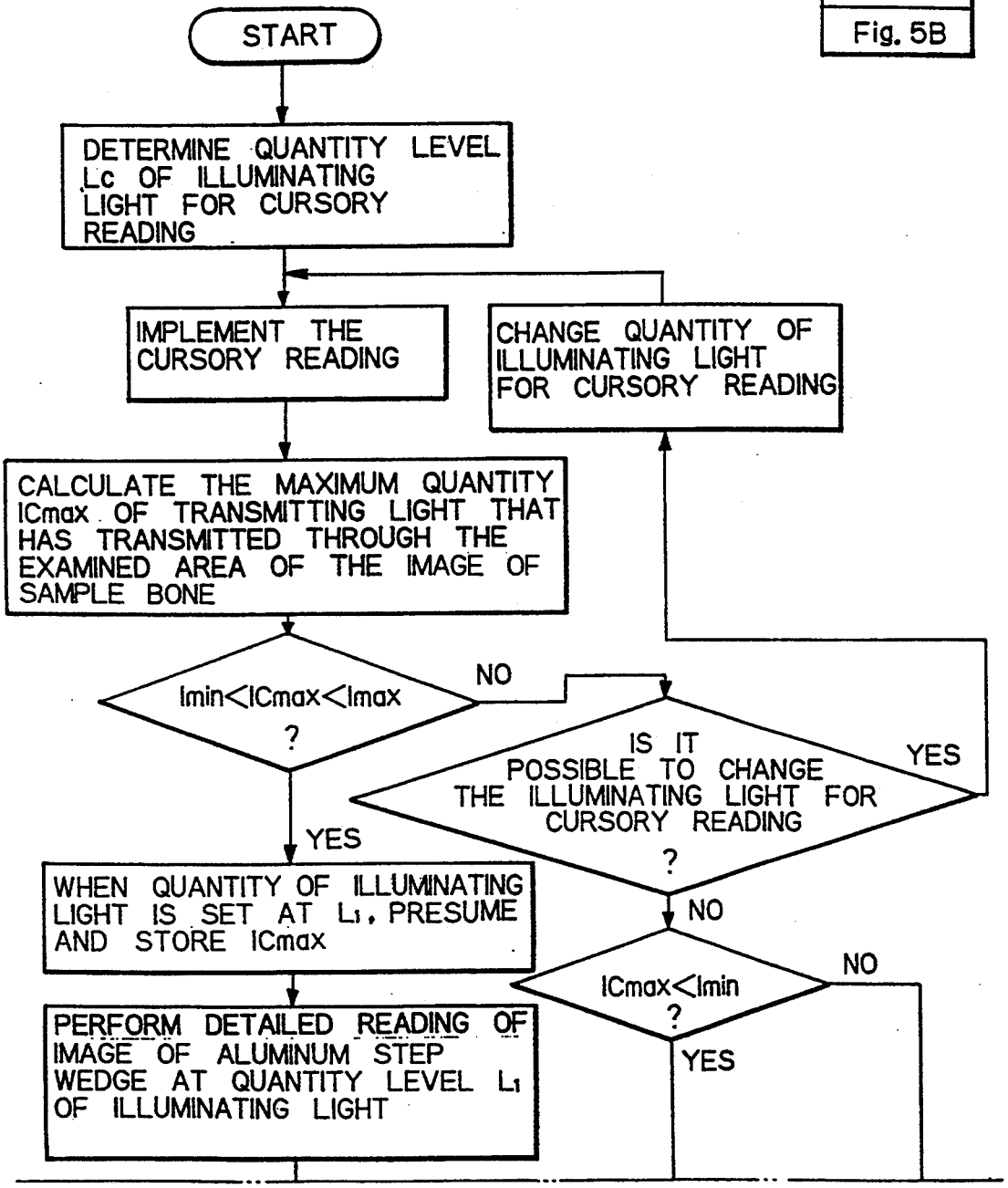

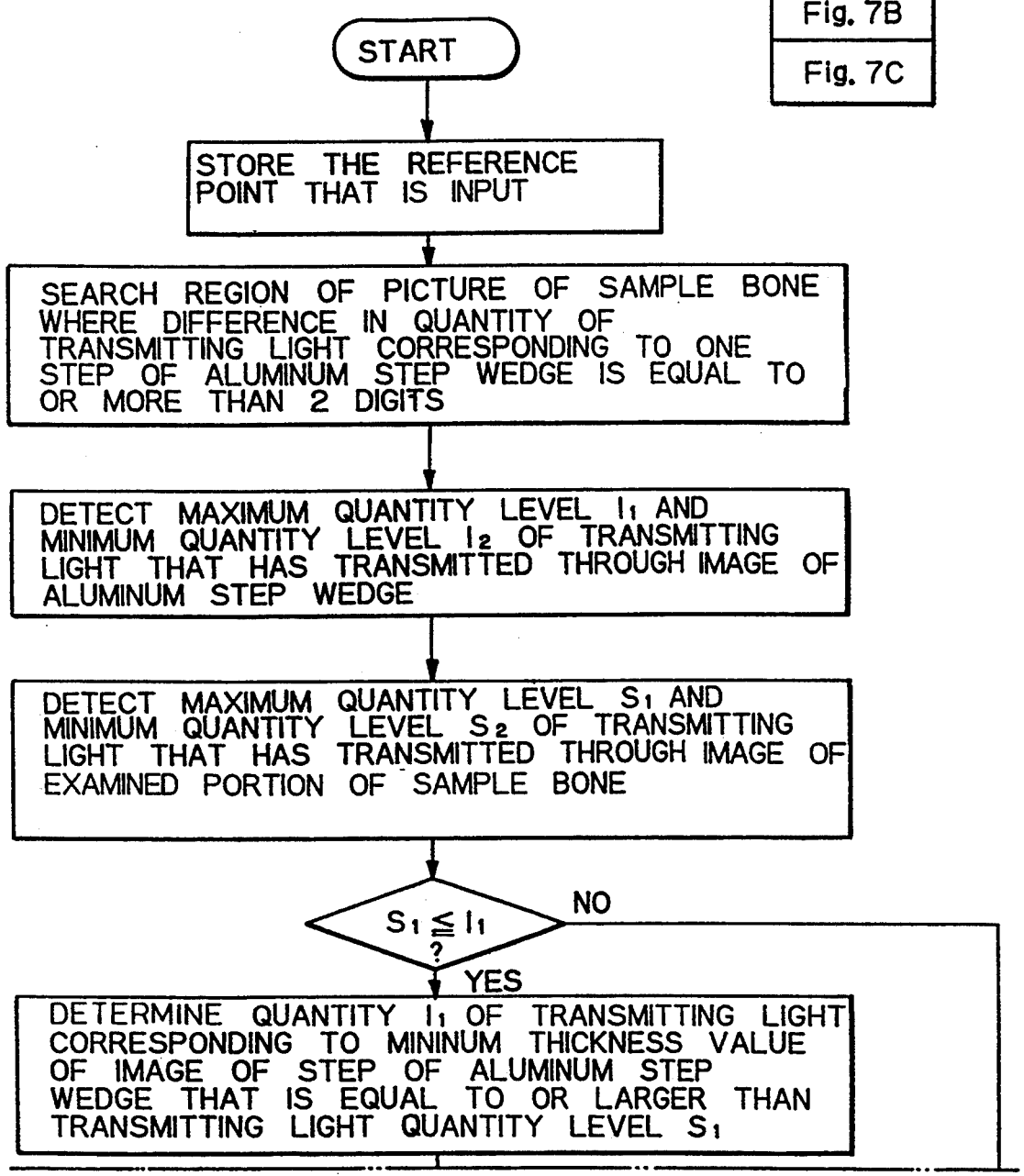

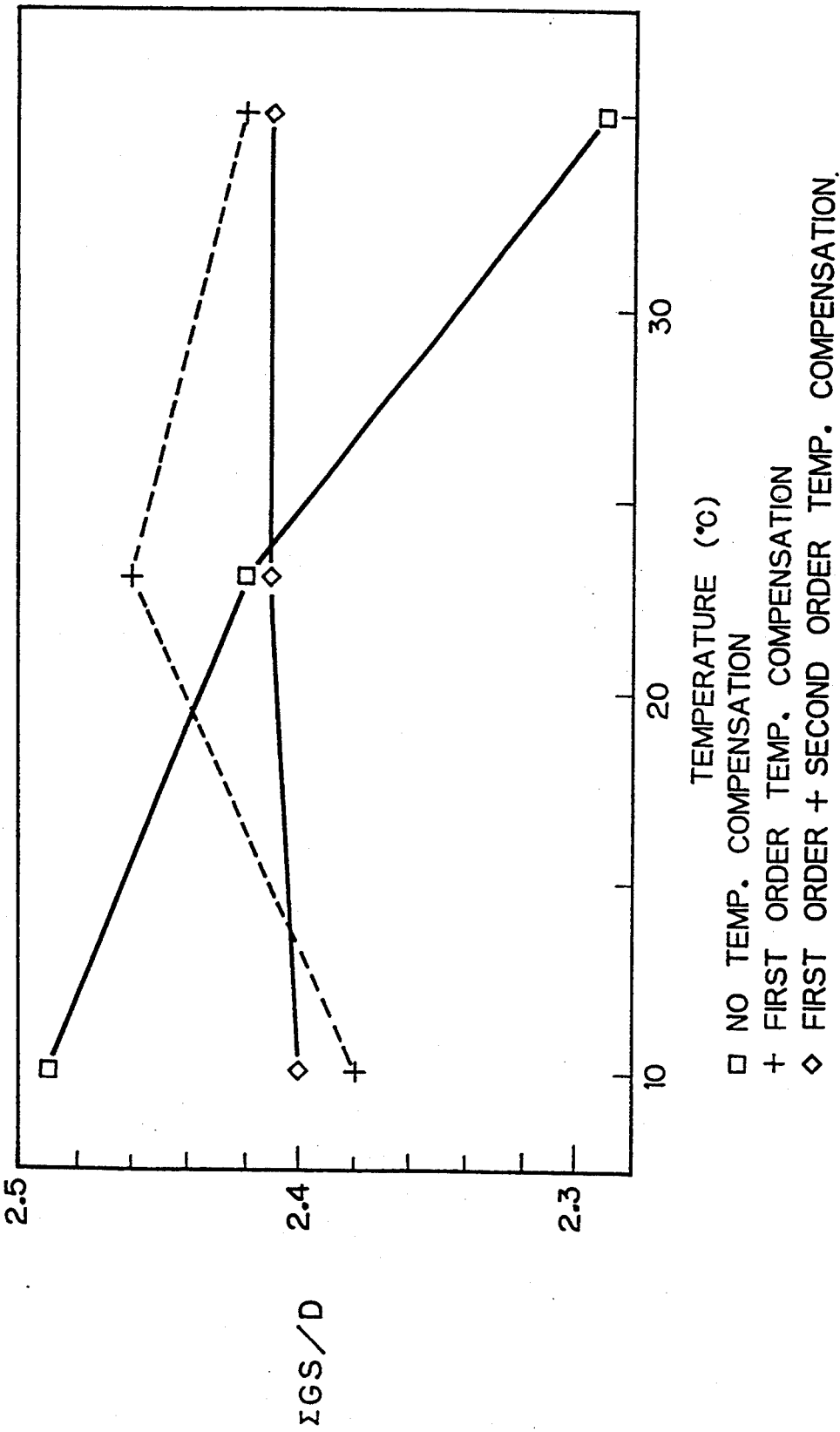

METHOD OF AND APPARATUS FOR BONE MEASUREMENT

BACKGROUND OF THE INVENTION

1. Field of the Invention

The present invention relates generally to an improvement in the detection and measurement of images or pictures in a film, such as an X-ray picture film, by illuminating the X-ray picture film with light. More particularly, it relates to a measurement of bones, especially human bones, by using an X-ray film having radiographical pictures of sample bones therein, for obtaining from an X-ray picture film various data, i.e., medical data. The present invention further relates to an improved method of and apparatus for measuring bone data such as morphometric data of bones, bone density data, and bone mineral content data by using a radiographical picture of bones in an X-ray picture film.

2. Description of the Related Art

A radiographical measurement of bones including bone morphometry is performed to evaluate the growth and aging of human bones, the diagnosis and confirmation of the rate of progress of bone diseases such as osteoporosis and osteomalacia, and the confirmation of the effect of treatments applied to various bone diseases.

The typical conventional methods for bone measurement are the microdensitometry (MD) method, and the photon-absorptiometry method. The former method measures the tone of the X-ray picture film of sample bones by a microdensitometer for bone measurement, and the latter method detects and measures the quantity of gamma rays, transmitting through sample bones, for bone measurement.

The MD method has become widely used because the method uses readily available X-ray picture film which can be easily obtained by an X-ray camera used widely for diagnosing bone fractures.

The photon absorptiometry method has, however, a drawback in that the use of the gamma-ray generator has not become as wide-spread as that of the X-ray camera.

Nevertheless, the above-mentioned microdensitometric bone measurement requires many manual work steps as described hereinbelow. Namely, when conducting conventional microdensitometric bone measurement or bone morphometry, a reference point for the bone morphometry is determined in the X-ray film of sample bones. Subsequently, an object region, such as a region on a line crossing the middle point of the longitudinal axis of the second metacarpal bone, is selectively measured by a predetermined procedure with reference to the reference point. The examined region is subsequently scanned by a microdensitometer so as to measure the intensity of light transmitting through the examined region, and the measured intensity of light transmitting through the region or the measured quantity of light absorbed by the region is recorded as a diagram on a chart. On the other hand, the X-ray radiography of a standard aluminum step block (it is hereinafter referred to as an aluminum step wedge), taken together with the X-ray radiography of the sample bones is scanned along its longitudinal axis by the microdensitometer, and the measured quantity of light transmitting through or absorbed by the aluminum standard step wedge is recorded as a different diagram on a chart. The diagram of the quantity of absorbed light is then converted by a digitizer into digital data to be inputted into an electronic computer to thereby convert the quantities of absorbed light at a plurality of points on the sample bones into corresponding gradations of the aluminum standard step block. The electronic computer then calculates and outputs various indices representing the bone morphology of the examined region on the basis of a pattern expressed by the gradations of the aluminum standard step wedge.

With the above-mentioned conventional MD method, the tone of the picture of the X-ray picture film of the sample bones is greatly dependent on both radiographying condition and developing condition to obtain the film, and the measurement of the X-ray picture film of the sample bone is impossible or, even if the X-ray picture film can be measured, the measured result includes large errors.

Further, when the pictures of the X-ray picture film are measured, an LED light source is often used for illuminating the X-ray picture film, and the light emitted by the LED light source and transmitting through or reflected from the film is usually detected by a CCD image sensor light detecting means. Nevertheless, the CCD image sensor is often adversely affected by the thermal conditions around the CCD image sensor. Namely, with an increase in temperature, the electric output, i.e., the voltage output delivered by the CCD image sensor subject to no input light increases as shown in FIG. 8. The voltage of the CCD image sensor under no-light conditions will be referred to as "an electric shielded output voltage" throughout the description of the specification, the accompanying claims, and the drawings of the present patent application. Since the electric shielded output voltage of the CCD image sensor is always superposed on an actual detecting output voltage of the CCD image sensor, such electric shielded output voltage brings about an error in the detecting and measuring operation of the CCD image sensor. Thus, it is important to provide an appropriate means for compensating for the electric shielded output voltage of the CCD image sensor during the measuring operation thereof.

SUMMARY OF THE INVENTION

An object of the present invention is to overcome the defects encountered by the conventional bone measurement methods such as the MD method and the photon absorptiometry method.

Another object of the present invention is to provide a method, and an apparatus, for achieving an accurate measurement of bone data such as bone morphometric data, bone density data, and bone mineral content data.

A further object of the present invention is to provide an improved method of bone morphometry by employing a process of adjustably changing the quantity of light generated by a light generating means and applied to an X-ray picture film of sample bones in response to a change in the tone of the X-ray picture film when a light transmitting through the X-ray picture film is measured for obtaining morphometric and other data of the sample bones.

A still further object of the present invention is to provide an apparatus for carrying out the above-mentioned improved method.

A further object of the present invention is to provide an apparatus for measuring bones employing a LED light source for illuminating an X-ray picture film and a CCD image sensor and provided with a temperature compensation means for compensating for an output error of the CCD image sensor due to a change in the environmental temperature under which the bone measurement is carried out, to thereby enhance the accuracy of the bone measurement operation and to obtain a wide dynamic range of the CCD image sensor.

In accordance with one aspect of the present invention, there is provided a bone measuring method, particularly a bone morphometric method in which a light is illuminated onto an X-ray film having therein both of simultaneously taken radiographic pictures of sample bones to be examined and of a given standard matter having a gradational thickness to detect a light transmitting through the pictures of the X-ray film, thereby using the detected quantity of the transmitting light for a measurement of said sample bone data, wherein the method is characterized by including the steps of:

selecting a given quantity Lc of light illuminating the pictures in the X-ray picture film, from a preset plurality of quantities of illuminating light;

applying the selected quantity Lc of illuminating light to the X-ray picture film for illuminating the pictures thereby allowing a cursory reading of the pictures in the X-ray picture film to obtain a cursory information of pixel of the pictures through detection of quantity of transmitting light that transmits through various regions of the pictures in the X-ray picture film;

determining a maximum quantity ICmax of transmitting light from the detected quantity levels of transmitting light transmitting through a predetermined examined region of the picture of the sample bones during the cursory reading of the pictures in the X-ray picture film;

applying a predetermined quantity $L_1$ of illuminating light to the X-ray picture film for illuminating the pictures thereof and for allowing the detailed reading of the picture of the given standard matter through detection of transmitting light that transmits through the picture of the given standard matter;

detecting a thickness $R_1$ of the standard matter which permits the illuminating light to transmit therethrough, a quantity level of the transmitting light being close to and more than the maximum quantity ICmax of light;

determining a quantity $I_{R1}$ of transmitting light that transmits through the picture of the standard matter at a portion thereof having a thickness $R_1$; and adjustably changing the quantity of illuminating light for illuminating the X-ray picture film until the obtained quantity $I_{R1}$ of transmitting light is close to a predetermined quantity level Imax of transmitting light without exceeding the predetermined quantity Imax of transmitting light.

In accordance with another aspect of the present invention, the above-mentioned bone measuring or bone morphometric method is further characterized by additionally including the steps of:

detecting a portion of the picture of the standard matter, in which portion a quantity of transmitting light that transmits through the portion satisfies a predetermined condition;

conducting a first judgement as to whether or not the quantity of transmitting light that transmits through a predetermined examined region of the X-ray picture film of the sample bones exists in quantity range of transmitting light that transmits through the detected portion of the picture of the standard matter;

conducting a second judgement as to whether or not quantity of transmitting light that transmits through said picture of the standard matter corresponding to quantity of transmitting light that transmit through the predetermined examined region of the picture of the sample bone is able to exhibit a resolving power satisfying a predetermined resolution; and further adjustably changing a quantity of illuminating light for illuminating said X-ray picture film on the basis of the second judgement.

The above-mentioned bone measuring method is further characterized by additionally including the step of conducting a third judgement as to whether or not a gradient value $\gamma$ in the predetermined examined region of the picture of the sample bone is equal to or larger than a predetermined gradient value regarding the X-ray picture film.

When the adjustment of the quantity of illuminating light is carried out so as to increase the quantity of illuminating light, it is desirable to initially detect a quantity I of transmitting light that transmits the picture of the standard matter, which quantity is close to and larger than the maximum quantity of transmitting light that transmits through the examined portion of the picture of the sample bone, and adjust the quantity of the illuminating light in a manner such that the quantity I of transmitting light is close to but does not exceed a predetermined value Imax.

On the other hand, when the adjustment of the quantity of illuminating light is carried out so as to decrease the quantity of illuminating light, it is desirable to detect a quantity $I_d$ of the transmitting light that transmits through a thickness portion $(R_1+\Delta R)$ thicker than the thickness $R_1$ of the standard matter obtained by the detailed reading of the standard matter, and set the quantity $I_d$ so as to be close to but not to exceed a predetermined value Imax.

In accordance with a further aspect of the present invention, there is provided an apparatus for measuring bone data by using an X-ray picture film having therein a radiographic picture of sample bones and a simultaneously taken picture of a given standard matter having a gradational thickness, and including:

a reading unit for reading the pictures by using a quantity of light that transmits through the pictures of the X-ray picture film illuminated by a given quantity of light;

a storing unit for storing the picture of the sample bone read by the reading unit;

an operation unit for calculating bone data of the picture of the sample bone stored in the storing unit; and an output unit for delivering the bone data calculated by the operation unit as bone measured output data, wherein the reading unit of the apparatus comprises in combination:

a light emitting unit for emitting the given quantity of light illuminating the X-ray picture film;

a light detecting unit for detecting a quantity of light that has transmitted through the X-ray picture film;

a unit for selecting a given quantity Lc of illuminating light for illuminating the pictures in the X-ray picture film, from a preset plurality of quantities of illuminating light;

a unit for applying the selected quantity Lc of illuminating light to the X-ray picture film for illuminating the pictures therein, and for permitting the light detecting means to implement a cursory reading of the pictures in the X-ray picture film for obtaining cursory information about pixels in the pictures through detection of quantity levels of transmitting light that transmits through various regions of the pictures in the X-ray picture film;

a unit for determining a maximum quantity ICmax of transmitting light from the detected quantities of light transmitting through a predetermined examined region of the picture of the sample bones during the cursory reading of the pictures in the X-ray picture film, the predetermined quantity $L_1$ of illuminating light being applied to the X-ray picture film for illuminating the pictures thereof thereby permitting the reading unit to implement a detailed reading of the picture of the given standard matter in the film through detection of light transmitting the picture of the given standard matter;

a unit for detecting a thickness portion $R_1$ of the standard matter which permits the illuminating light to transmit therethrough, the quantity of the transmitting light that transmits through the thickness portion of the standard matter being close to but more than the maximum quantity ICmax of light;

a unit for determining a quantity $I_{R1}$ of light that transmits through the picture of the standard matter at a portion thereof having a thickness $R_1$;

a first light adjusting unit for adjustably changing a quantity of illuminating light emitted by the light emitting unit and illuminating the X-ray film until the obtained quantity $I_{R1}$ of transmitting light is close to a predetermined quantity Imax of transmitting light without exceeding the predetermined quantity Imax of transmitting light;

a region detecting means for detecting a portion of the picture of the standard matter, in which portion a quantity of transmitting light that transmits through the portion satisfies a predetermined condition;

a first judgement unit for conducting a first judgement as to whether or not the quantity of transmitting light that transmits through a predetermined examined region of the X-ray picture film of the sample bones exists in quantity range of transmitting light that transmits through the detected portion of the picture of the standard matter;

a second judgement unit for conducting a second judgement as to whether or not the quantity of transmitting light that transmits through the picture of the standard matter corresponding to quantity of transmitting light that transmit through the predetermined examined region of the picture of the sample bone is able to exhibit a resolving power satisfying a predetermined resolution; and a second light adjusting unit for further adjustably changing a quantity of illuminating light emitted by said light emitting unit and illuminating the X-ray picture film on the basis of the second judgement.

In the above-described apparatus, the reading unit further comprises a unit for determining whether or not a gradient value $\gamma$ in the predetermined examined region of the picture of the sample bone is equal to or larger than a predetermined gradient value regarding the X-ray picture film.

BRIEF DESCRIPTION OF THE DRAWINGS

The above and other objects, features and advantages of the present invention will be made more apparent from the ensuing description of the preferred embodiments thereof in conjunction with the accompanying drawings wherein:

FIGS. 5A and 5B are flow charts illustrating a preparatory process carried out by the bone measurement method and apparatus of the present invention, including a preparatory process for adjustably changing an intensity of illumination of the light illuminating the X-ray film;

FIGS. 7A, 7B and 7C are flow charts illustrating the judging process and the illumination adjustment process, used with the bone measuring method and apparatus of the present invention;

FIG. 14 is a graph illustrating an effect of the compensation according to the present invention.

DESCRIPTION OF THE PREFERRED EMBODIMENTS

The radiographic picture, of e.g., sample bones in an X-ray picture film, used with the present invention can be detected as a difference in the tone of blackness and the outlined shape indicating the shape of the sample bones formed in the X-ray picture film. As a standard matter having different regularly arranged thicknesses portions an aluminum block having many steps (it is referred to as an aluminum step wedge) is used. A tapered aluminum block (aluminum slope) may be used instead of the aluminum step wedge. As sample bones used for forming a high-contrast X-ray picture, human bones having a uniform, thin layer of soft tissues, are desirable. Desirable bones are bones of the hand, and long bones, such as humerus, radius, ulna, femur, tibias, and fibula. The second metacarpal bone is practically most desirable. Cancellous bones, such as calcaneus, vertebra and epiphyses of long bones may be used as sample bones. The calcaneus is practically most desirable.

Figure 1:
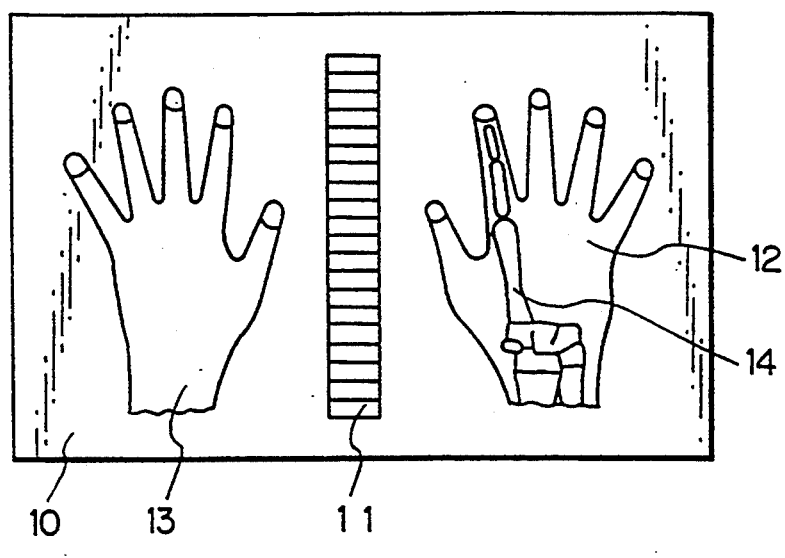
FIG. 1 is a schematic plan view illustrating how to arrange radiographed objects, i.e., sample bones and a standard step matter for obtaining an X-ray picture film that is used for conducting the bone measurement according to the present invention.

FIG. 1 illustrates an arrangement of sample bones, i.e., bones of the hand, and an aluminum step wedge on a taking plane suitable for radiographying by X-ray. In FIG. 1, a right hand 12, a left hand 13 and an aluminum step wedge 11 are placed on an X-ray plate 10 for producing a X-ray picture film therefrom, and the second metacarpal bone 14 of the right hand 12 is typically shown.

Figure 2:
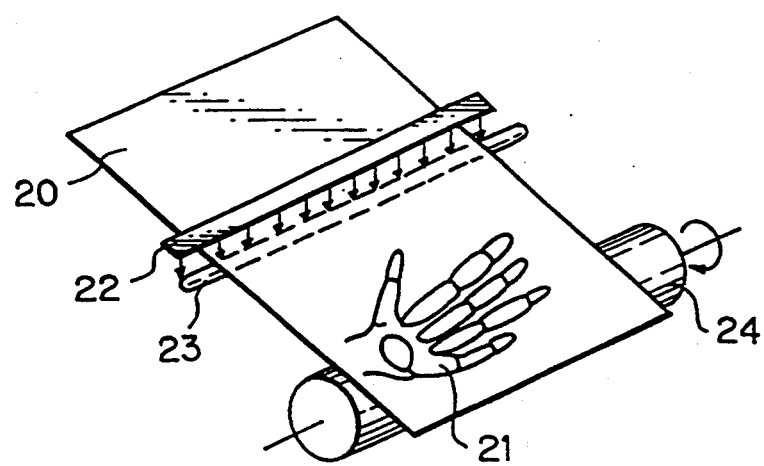
FIG. 2 is a schematic view of an automatic reading means of an bone measurement apparatus according to the present invention.

The produced X-ray picture film is automatically read by an automatic reading means for the bone measurement, as schematically shown in FIG. 2.

Referring to FIG. 2, the X-ray picture film designated at 20 and having therein a picture 21 of the right hand bone is illuminated by a light emitted from a light source 22 in the form of a strip-like element having a plurality of light emitting elements (LED) arranged linearly. A contact type image sensor 23 typically consisting of a known charge coupled device (CCD) is arranged on the opposite side to the light source 22 with regard to the X-ray picture film 20, and is in approximate contact with the rear face of the X-ray picture film 20 that is linearly conveyed through the light source 22 and the image sensor 23 by a feed roller 24. The image sensor 23 detects and measures a light that has transmitted through the X-ray picture film 20, and generates electric output signals indicating a quantity of the transmitting light. The electric output signal is sent, via an analogue to digital converter, to a processing unit consisting of a known micro-processing unit provided with a function of analytical measurement of the sample bones.

Figure 5B:
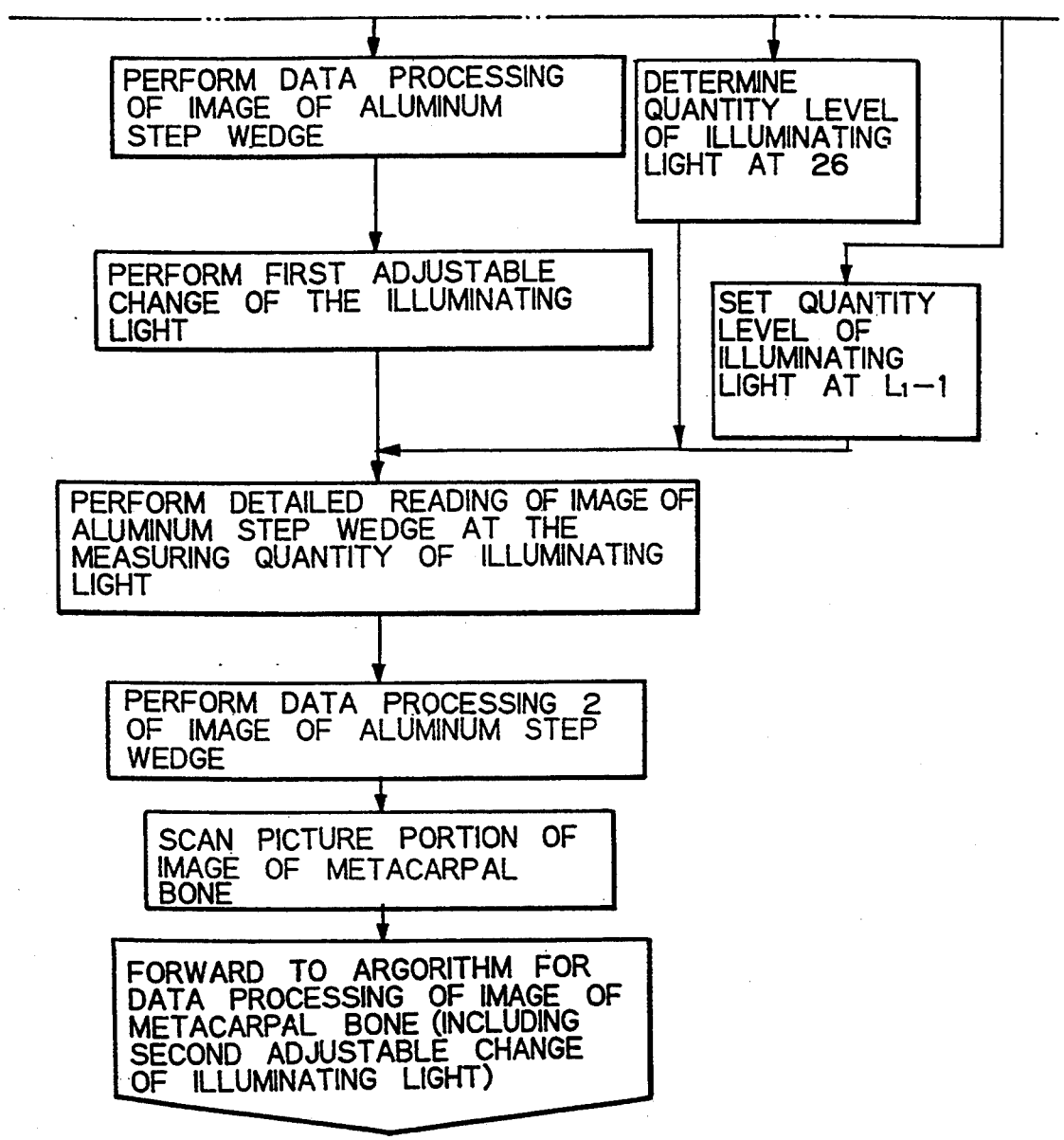

FIG. 5 illustrates a flow chart of the bone measurement process according to a preferred embodiment of the present invention and conducted by the processing unit.

As shown in the flow chart of FIG. 5, the first step of the bone measurement by using the X-ray picture film includes sub-steps of manually selecting a quantity Lc of light for illuminating the X-ray film ( the X-ray picture film 20 of FIG. 2 ) from a plurality of preliminarily prepared quantities of illuminating light by inspecting the radiographic condition of the X-ray picture film, applying the selected quantity Lc of illuminating light to the X-ray picture film, and detecting a quantity of light that transmits through the X-ray picture film as a kind of rough information regarding rough picture elements of the pictures in the X-ray picture film. The above subsidiary step of detecting the quantity of light that transmits through the pictures of the X-ray picture film can be considered as a subsidiary step of conducting a cursory reading of the pictures of the X-ray picture film by scanning the X-ray picture film with the illuminating light having the above-mentioned quantity level Lc.

Subsequently, a step of designating a given portion of the picture of the aluminum step wedge 11 (FIG. 1) and of an examined region of the picture of the sample bones 14 is implemented on the basis of the data of the aforementioned cursory reading of the pictures in the X-ray picture film, to thereby conduct a detailed reading of the designated portion of the aluminum step wedge 11 and of the examined region of the sample bone 14 in the X-ray picture film.

At this stage, it is to be noted that the PCT Application PCT/JP 90/00220 filed by the same Assignee as the present case on Feb. 23, 1990 and designating the United States and EPC discloses the method of cursory reading of pictures of the X-ray picture film in more detail.

In the subsequent step, a calculation for obtaining a maximum quantity ICmax of the transmitting light that can be an information of rough picture elements within a predetermined portion of the examined region of the picture of the sample bones 14 is performed.

From experimental analysis of many kinds of X-ray picture films, it was already confirmed that the predetermined portion of the examined region 14 for obtaining the maximum quantity ICmax of the transmitting light should desirably be, for example, a rectangular-shape region having approximately 2.3 mm width, and 7 mm height with the examined region at the center thereof when the examined region is designated as a middle portion of the sample bones 14, i.e., the second metacarpal bone illustrated in FIG. 1. Of course, the above-mentioned predetermined region for obtaining the maximum quantity ICmax of the transmitting light may be changed to a different portion of the examined region of the sample bone picture in the X-ray picture film depending on the shape and measuring method of the examined region as long as similar experimental analysis of the X-ray picture film is preliminarily performed.

When the predetermined portion of the examined region for obtaining the maximum quantity ICmax is determined, a comparison of an extent of such predetermined portion for ICmax with predetermined values Imax and Imin corresponding to the maximum and minimum light quantity values in a range capable of being analyzed by an employed image sensor. For example, the values of Imax and Imin are preliminarily set at 50 and 30, respectively by considering the maximum and minimum values 250 and 0 that can be subjected to A/D conversion by an employed A/D converter.

When compared, and when the predetermined portion of the examined region for obtaining ICmax is detected to be larger than Imin and smaller than Imax, the maximum quantity ICmax of the transmitting light is finally determined regarding a predetermined quantity $L_1$ of the illuminating light to be used for the cursory reading of the pictures in the X-ray picture film, from the later-described Table 1 indicating the relationship between the illuminating light and the illuminating time period, and is stored in the memory of the processing unit.

At a subsequent step, the picture of the standard matter i.e., the aluminum step wedge 11 is scanned by the predetermined quantity $L_1$ of the illuminating light, and simultaneously, a quantity of the light transmitting through the aluminum step wedge 11 is detected and measured to obtain an information of the minute picture elements of the picture of the standard matter in the X-ray picture film. In this step, an edge portion of the aluminum step wedge picture is automatically detected in the manner described in the afore-mentioned PCT Application No. PCT/JP 90/00220, to thereby gather data with regard to a relationship between a position on and a thickness of the aluminum step wedge 11.

After the completion of the above-mentioned step of gathering the data of the aluminum step wedge, a preparatory adjustment of the quantity of illumination light is performed as a first time adjustment of the illuminating light. The detailed process of the first time adjustment of the illuminating light is illustrated in the flow chart of FIG. 6.

Figure 6:
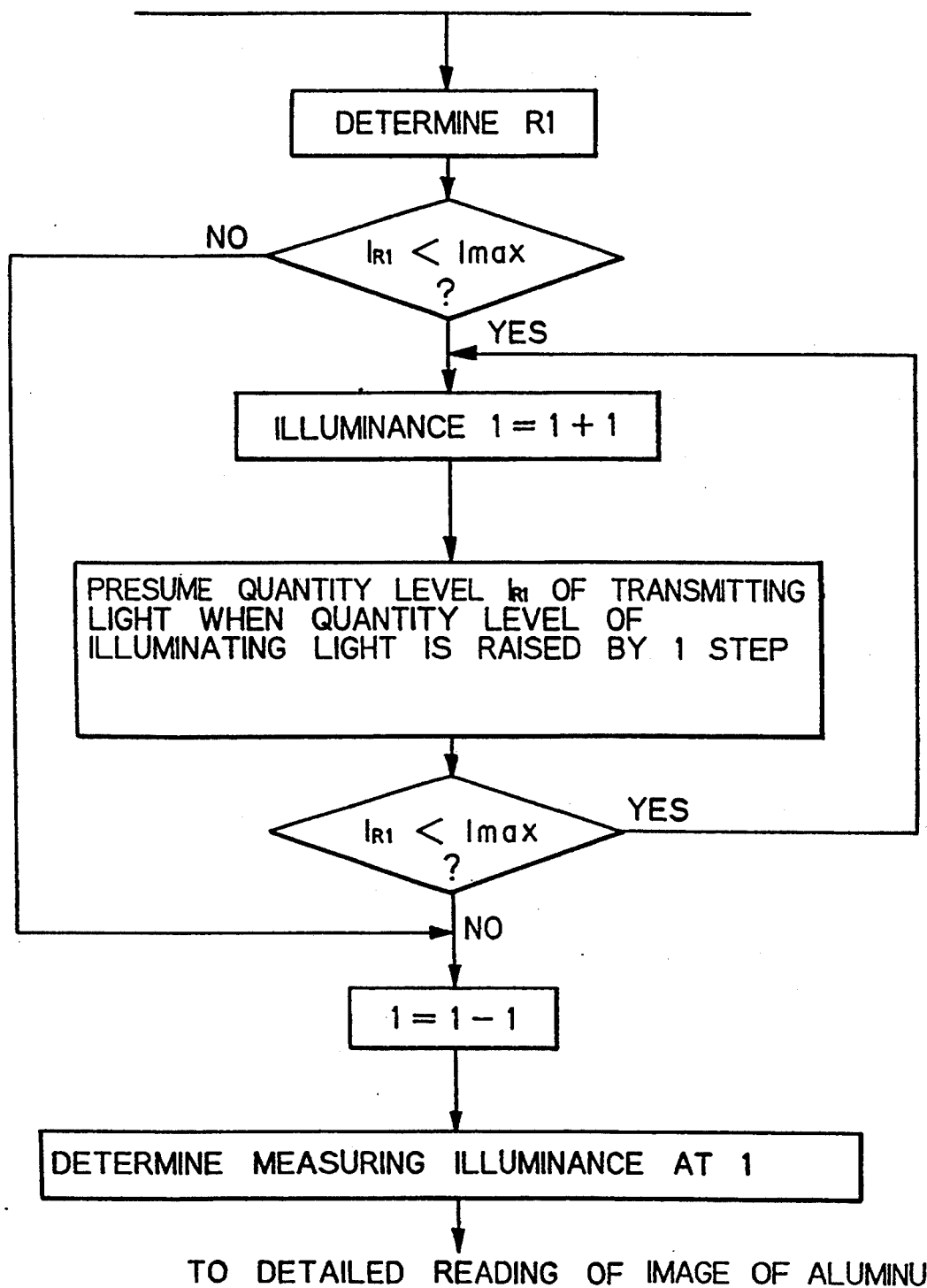
FIG. 6 is a flow chart particularly illustrating the process for conducting the preparatory adjustment of the illumination intensity of the light illuminating the X-ray film.

As will understood from the flow chart of FIG. 6, a thickness $R_1$ of the aluminum step wedge 11 is initially determined on the basis of the above gathered data of the aluminum step wedge 11. Namely, the thickness $R_1$ is determined so that the quantity of light transmitting through the aluminum step wedge at a step portion having that thickness $R_1$ is close to and larger than the quantity ICmax of the transmitting light. Subsequently, the process of obtaining a correct quantity $I_{R1}$ of transmitting light that transmits through the aluminum step wedge 11 at the step portion having the thickness $R_1$ is performed. The obtained quantity $I_{R1}$ of the transmitting light is then compared with Imax. When the former $I_{R1}$ is smaller than Imax, the illumination set value l is increased to (l+1) based on the relationship shown in Table 1, to thereby presume a different proportional quantity $I_{R1}$ of the transmitting light in the case where the time period of the illumination light is prolonged. The presumed quantity $I_{R1}$ of transmitting light is now compared with Imax in order to determine whether or not the quantity $I_{R1}$ is still smaller than the latter value Imax. The presumption and comparison steps are repeated until the presumed quantity $I_{R1}$ of transmitting light becomes larger than Imax, and when such condition is achieved, a quantity l of the corresponding illuminating light is determined. Then, a lower quantity l−1 of the illuminating light is eventually determined as a quantity l of the illuminating light to be used for the bone measurement.

When either ICmax is smaller than lmin or ICmax is larger than Imax, a checking process for finding whether or not there exists a quantity of the illuminating light in the plurality of predetermined quantities of illuminating light, which is able to satisfy an equality condition such that Imin<ICmax<Imax, is performed.

If there exists such quantity of illuminating light, the quantity of illuminating light used for carrying out the cursory reading of the picture of the X-ray picture film is appropriately changed, and the cursory reading process is repeated.

If there does not exist the above-mentioned quantity of illuminating light, the afore-mentioned first time adjustment of the illuminating light is not performed, and the illuminating light quantity is set at the possible maximum quantity of illuminating light, if ICmax is smaller than Imin. If ICmax is larger than Imax, the quantity of illuminating light for the measurement purpose is set at ($L_1$−1), and the detailed reading of the aluminum step wedge 11 is carried out by using the light for the measurement purpose.

When the detailed reading of the aluminum step wedge 11 by the illuminating light for the measurement purpose and the data processing for the aluminum step wedge are completed (see FIG. 5), the picture of the second metacarpal bone in the X-ray picture film is scanned by the illuminating light for the measurement purpose. Thereafter, an algorithm is used to process the data of the metacarpal bone including later-described first and second judgement processes as well as the process of a second adjustment of the illuminating light quantity.

In principle, the first and second judgements are carried out in the manner described below. Namely, with regard to the standard matter in the X-ray picture film, detection of a region thereof where the quantity of the transmitting light satisfies a predetermined condition of the quantity of light is initially conducted, and subsequently, a process of obtaining the range of quantity of light transmitting through the detected region of the standard matter, i.e., the aluminum step wedge is implemented. Then, the first judgement as to whether or not the range of quantity of light transmitting through the examined region of the picture of the sample matter, i.e. the sample bones, is within the obtained range of quantity of light transmitting through the standard matter is conducted.

Further, the second judgement as to whether or not the quantity of light transmitting the picture of the standard matter, which corresponds to that of light transmitting through the examined region of the picture of the sample bone is able to exhibit a predetermined resolving power, respectively is conducted, and on the basis of the second judgement, the second time adjustment of the quantity of light illuminating the X-ray picture film is performed.

Figure 7B:
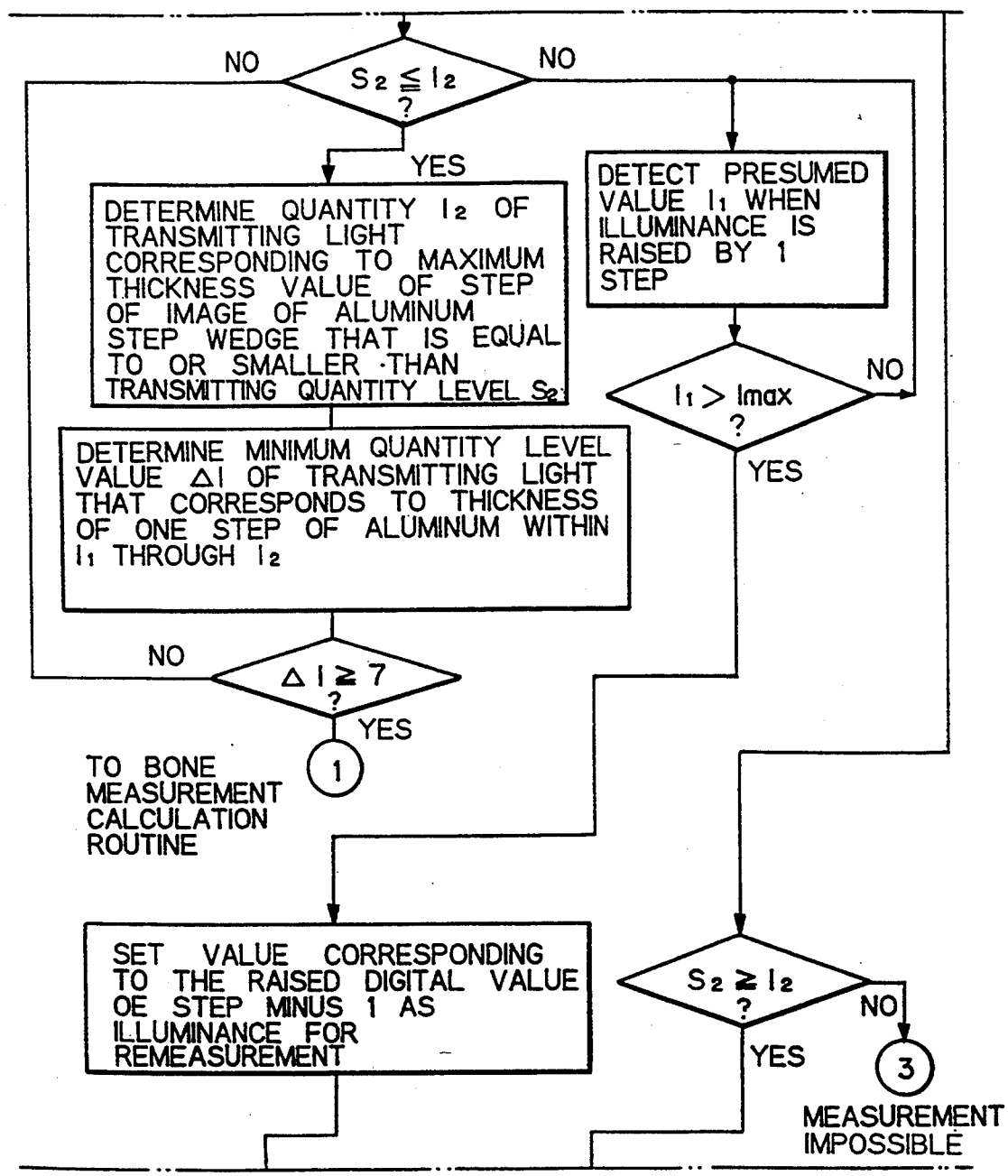
Figure 7C:
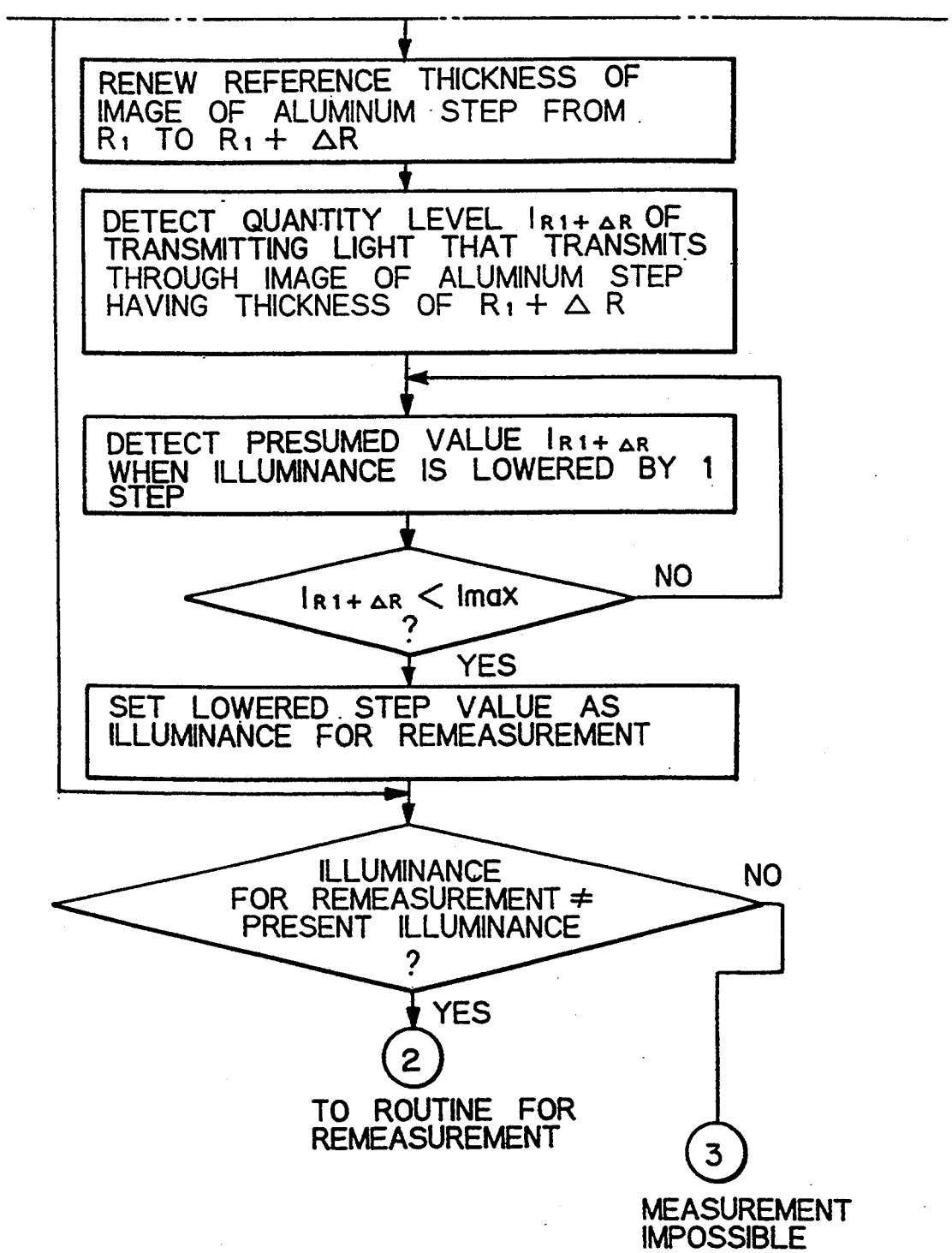

A typical example of the above-mentioned first and second judgements and the second time adjustment of the quantity of illuminating light is clearly shown in FIG. 7.

As illustrated in FIG. 7, when the picture of the aluminum step wedge in the X-ray picture film conveyed to a predetermined position is illuminated by a predetermined quantity of light, a quantity of light transmitting through the picture of the aluminum step wedge is detected and measured.

From the relationship between the detected quantity of transmitting light and the thickness of the aluminum step wedge, a range of quantity level of transmitting light regarding the picture of the aluminum step wedge that is capable of being effectively used as standard steps i.e., a picture region provided with a plurality of separate steps is determined.

It should be understood that when a given region of the picture of the aluminum step wedge is required to be effectively measured as standard steps, a given quantity of light transmitting through the region must include a plurality of quantitative components of transmitting light, which components are different from one another by more than two digits after the A/D conversion thereof into respective digital values by an analogue to digital converter (A/D converter), in view of a bit error of the A/D converter. Of course, the quantity of light transmitting the aluminum step wedge and measured by the light sensing unit (CCD) should not saturate the CCD.

After the above-mentioned detection of the effectively usable region of the picture of the aluminum step wedge, the quantity of light transmitting through the thickest step portion of the usable region is defined as $I_1$, and the quantity of light transmitting through the least thick step portion of the usable region is defined as $I_2$. Further, the maximum quantity of light transmitting the examined region of the sample bones is defined as $S_1$, and the minimum quantity of light transmitting through the examined region of the sample bones is defined as $S_2$.

Now, a first step judgement as to whether or not $S_1$ is equal to or less than $I_1$ is performed. If not, the quantity of light illuminating the X-ray picture film must be reduced. If yes, a second step judgement as to whether or not $S_2$ is equal to or larger than $I_2$ is performed. As a result, if not, the quantity of light illuminating the X-ray picture film is increased. Nevertheless, it should be understood that is $S_1$ is larger than $I_1$, and if $S_2$ is smaller than $I_2$, it is impossible to conduct the measurement even if the quantity of light illuminating the X-ray picture film is adjustably varied. In this case, the X-ray picture film should preferably be delivered from the roller conveyer after presenting an indication on the X-ray picture film that the measurement is impossible.

When both conditions of $S_1 \leq I_1$, and $S_2 \geq I_2$ are satisfied, the second judgement is conducted. Namely, a process of detecting a quantity $I_1'$ of light transmitting through the aluminum step wedge, which is preferably closest to and larger than the quantity $S_1$ of transmitting light is conducted. Also, another process of detecting a quantity $I_2'$ of light transmitting through the aluminum step wedge, which is preferably closest to and smaller than the quantity $S_2$ of transmitting light is conducted. Subsequently, within the light quantity range from $I_1'$ through $I_2'$, respective digital values after the A/D conversion which represent differences in the thickness regarding between two neighboring steps of the aluminum step wedge are detected, and the smallest value is defined as $\Delta I$. For example, when a difference in the thickness of the neighbouring steps of the aluminum step wedge is 1 mm, and as an accuracy in the measurement, a resolving power of less than 0.2 mm is required, the digital value of the thickness of each step must be larger than 5 digits, preferably larger than 7 digits. If the value must be larger than 7 digits, a judgement as to whether or not the $\Delta I$ is equal to or larger than 7 is conducted. As a result of the judgement, if it is satisfied that the $\Delta I$ is equal to or larger than 7, it is further judged that the current quantity of light illuminating the X-ray picture film is appropriate, and the entire process of the bone measurement is successively conducted. Nevertheless, if the above condition is not satisfied, it is necessary to conduct an operation for increasing the current quantity of light illuminating the X-ray picture film.

At this stage, a description of an explanation of how to change a quantity of light illuminating the X-ray picture film is provided below.

When it is detected that the current quantity of illuminating light applied to the X-ray picture film is too low, an adjustment of the quantity of illuminating light is performed in such a manner that the quantity $I_1'$ of light transmitting through the picture of the aluminum step wedge is made preferably closest to but does not exceed the predetermined quantity Imax, and the bone measurement is conducted on the basis of the adjusted quantity of illuminating light. At this stage, the above-mentioned predetermined light quantity Imax is set at between 95% and 98% of the saturated level of the sensor unit or the A/D converter.

On the other hand, when it is detected that the current quantity of illuminating light applied to the X-ray picture film is excessive, a quantity Id of light transmitting through one of the steps of the aluminum step wedge, i.e., the step having a thickness that is thicker than a given thickness $R_1$ by a predetermined thickness $\Delta R$ is then detected. Namely, the quantity Id of light that transmits throught the step ($R_1+\Delta R$) of the aluminum step wedge is detected. Then, an adjustment of the current quantity of illuminating light is conducted in such a manner that the detected quantity Id of transmitting light is made preferably closest to but does not exceed the predetermined quantity Imax, and the bone measurement is conducted on the basis of the adjusted quantity of illuminating light. At this stage, the above-mentioned predetermined light quantity Imax is set at between 95% and 98% of the saturated level of the sensor unit or the A/D converter.

In this case, the thickness $\Delta R$ should preferably be set at 1 mm, if a difference in the thickness of the two neighbouring steps of the aluminum step wedge is 1 mm.

When it is detected that the adjusted quantity of illuminating light does not differ from the current quantity of illuminating light, the bone measurement is stopped for curtailing of measuring time. Then, the X-ray picture film is delivered from a measuring apparatus after providing an appropriate indication of an incapacity of measurement on the X-ray picture film.

In the method of the present invention, a third judgement may be performed to carry out an adjustment of the illuminating light, as required, by using a value of "$\gamma$" indicating the gradient of a picture in a photographic or radiographic film such as an X-ray picture film as used with the bone measurement of the present invention, and defined by the equation (1) below.

$$\gamma = \text{a variation in absorbance (OD)/a variation in a relative exposure} \quad (1)$$

Namely, concerning respective picture regions $I_1'$ and $I_2'$ of the aluminum step wedge in the X-ray picture film, detection of the values "$\gamma_i = I_1'$ through $I_2'$" for respective steps is initially carried out, and only when the minimum one of the detected values "$\gamma_i$" is beyond a predetermined value "$\gamma_0$", is it possible to accurately measure the pictures of the X-ray picture film. Therefore, the detection of the value "$\gamma_i$" can be used in combination with the above-mentioned judgement of the resolving power. Generally, the above-defined value "$\gamma$" should preferably be a value between 1 through 4, and the value "$\gamma_0$" should be a value between 1.0 and 2.0.

Adjustment of the illuminating light may be accomplished by adjustably changing the time period of illumination of light in place of adjusting the intensity of illuminating light. For example, when a strip-like light emitting device (LED) is used as a light generating means, and when a line sensor comprised of a charged coupled device (CCD) is used as a light sensing means for detecting a transmitting light, it is possible to adjust the time period of the illuminating light through a control of the number of pulse-operated elements of the LED by using a pulse generator.

In the present invention, if a reading means employing LED and CCD is used, compensation for a change in the operation characteristics of the reading means such as a change in the sensitivity, and a change in the illumination due to the lapse of time may be needed for cancelling adverse effect of the change of the operation characteristics of the reading means on the result of the bone measurement. In such case, an adjustment of the time period of illumination instead of an adjustment of the intensity of the illuminating light may be effectively used to improve the above-mentioned compensation effect from the view point of practical measurement.

TABLE 1

| The Setting Value of Illumination | The Time Period of Illumination |
| --- | --- |
| 1 | 128 |
| 2 | 256 |
| 3 | 384 |
| 4 | 512 |

TABLE 1-continued

| The Setting Value of Illumination | The Time Period of Illumination |
|---|---|
| 5 | 640 |
| 6 | 768 |
| 7 | 896 |
| 8 | 1,024 |
| 9 | 1,152 |
| 10 | 1,280 |
| 11 | 1,536 |
| 12 | 1,792 |
| 13 | 2,048 |
| 14 | 2,304 |
| 15 | 2,560 |
| 16 | 3,072 |
| 17 | 3,584 |
| 18 | 4,544 |
| 19 | 5,568 |
| 20 | 6,592 |
| 21 | 7,616 |
| 22 | 9,088 |
| 23 | 11,136 |
| 24 | 13,632 |
| 25 | 15,680 |
| 26 | 18,176 |

Figure 3:
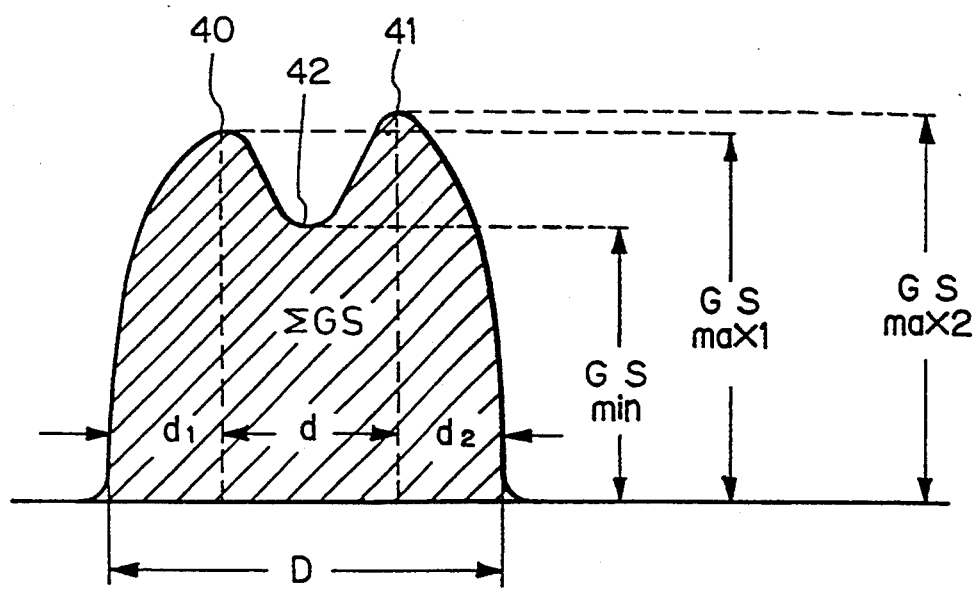
FIG. 3 is a schematic and graphical view illustrating a calculation theory used for the bone measurement, and practiced by a bone measuring apparatus according to the present invention.

FIG. 3 illustrates a pattern representing the various thicknesses of the aluminum step wedge which correspond to a variety of quantities of light transmitting through various points on a transverse line crossing the middle point of the longitudinal axis of the picture of the second metacarpal bone. Namely, it is possible to understand the concrete calculating operations conducted during the bone measurement of the present invention.

In FIG. 3, D is the width of the bone, a hatched area expresses bone density, $d_1$ and $d_2$ are the widths of bone cortices, d is the width of the bone marrow, $GS_{min}$ corresponds to the minimum value of a valley 42 between peaks 40 and 41 and is the index of the density of (the bone cortex)+(the bone marrow), GS max1 and GS max2 are the respective maximum values of peak portions, and $\Sigma GS$ is the total area of the hatched area with respect to the bone width D. It should be understood that the values GS max2 etc. indicate differences in the steps of the aluminum step wedge corresponding to differences in the quantities of transmitting light that transmits through the examined region of the picture of the sample bone in the X-ray picture film, via a difference in the thickness of the aluminum step wedge.

A concrete example of the calculating method employed by the bone measurement may be the same as that employed by the bone measurement using the known MD method, as disclosed in e.g., U.S. Pat. No. 4,721,112 which corresponds to the Japanese unexamined Patent Application Publication (Kokai) No. 61-109557. When the pictures of the sample bone and the standard matter before measured by the CCD sensing unit are directly stored in the memory, it may be possible to use a calculating means for conducting a calculation to convert the sample bone picture into the corresponding aluminum step wedge thickness.

The calculation for the bone measurement, performed by the calculating means may be such as disclosed in U.S. Pat. No. 4,721,112 which performs the bone morphometry of regions of a long bone and determines the bone density distribution of the long bone on the basis of the measured results.

An apparatus for the bone measurement of the present invention is characterized by being provided with an arrangement for executing the afore-described bone measuring method of the present invention.

Figure 4:
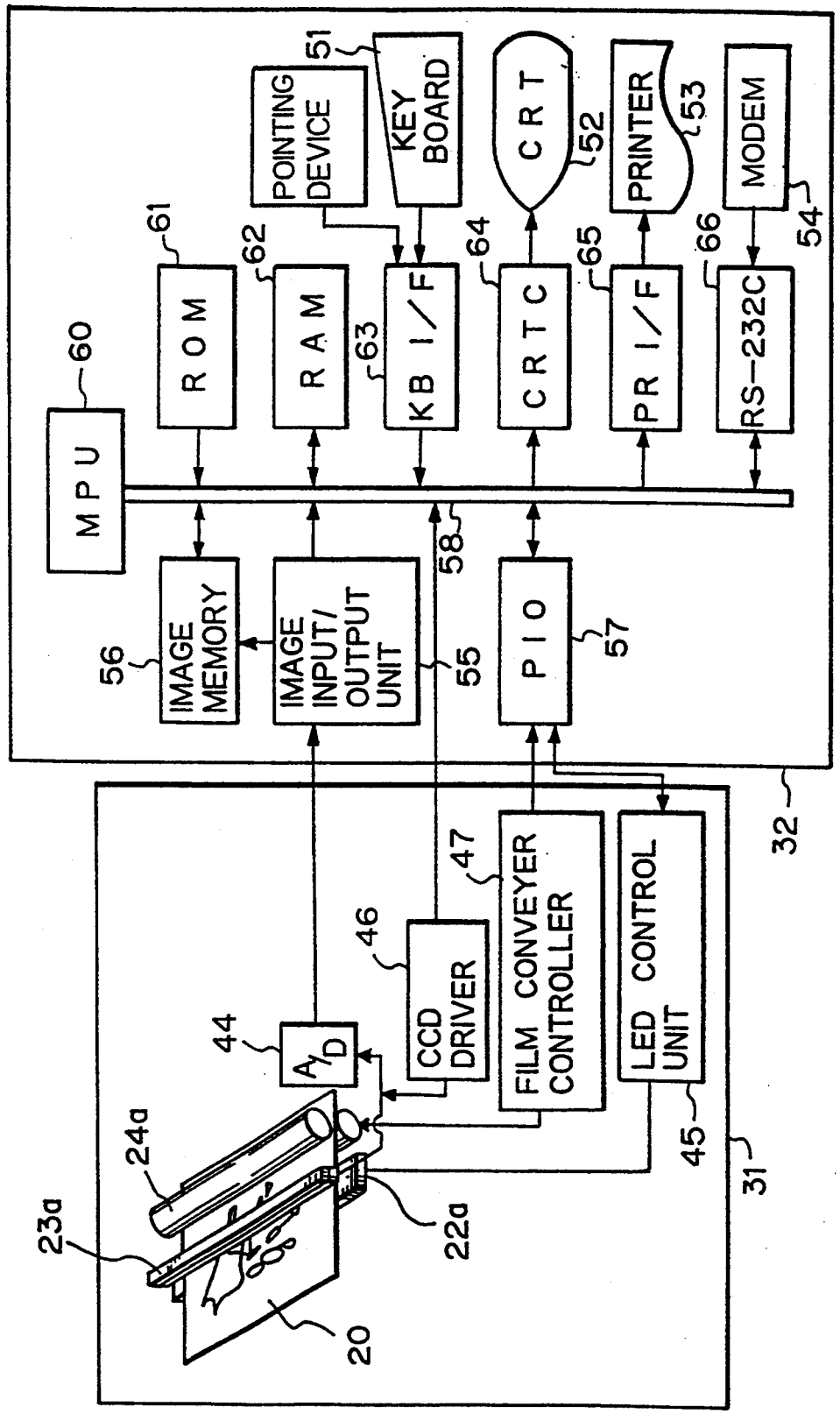
FIG. 4 is a block diagram schematically illustrating a bone measurement apparatus in which an illumination light adjustment means according to the present invention is incorporated.

FIG. 4 schematically illustrates a preferred embodiment of the bone measurement apparatus which includes an automatic reading function unit 31 provided with a light generating means (LED) 22a for emitting a light illuminating the X-ray picture film 20, a light detecting means (CCD) 23a for detecting an intensity of light that has transmitted through the X-ray picture film 20, a film conveyer means 24a for automatically conveying the X-ray picture film 20 through the light generating means 22a and the light detecting means 23a, an A/D converter 44 connected to the light detecting means 23a, a LED driver 45 connected to the light generating means 22a, a CCD driver 46 connected to the light detecting means 23a, and a film feed controller connected to the film conveyer means 24a.

The bone measurement apparatus of FIG. 4 is further provided with a bone measurement data processing unit 32 described later.

The typical example of the light generating means 22a of the automatic reading function unit 31 may be comprised of a spot-light emitting means provided with an appropriate scanning means to scan the spot-light onto the surface of the X-ray picture film 20. Nevertheless, a band-like light source means, i.e., LED capable of constantly emitting a band-like light onto the surface of the X-ray picture film 20 and needing no light-scanning means is appropriate from the view point of not only practical use and but also reduction in the size of the whole apparatus.

The light detecting means 23a may be any type of light sensing means capable of detecting a transmitting light and of measuring an intensity of the transmitting light. However, when the above-mentioned band-like light source means (LED) is used for illuminating the X-ray picture film 20, a corresponding band-like light detecting means such as a conventional line sensor should be preferably used, and a conventional band-like contact image sensor formed by a charge coupled device (CCD) is best from the view point of practical use.

The film conveyer means 24a may be comprised of a conventional roller means which preferably includes a pair of drive and pinch rollers conveying a film therebetween. The film conveyer means 24a may be of another appropriate conveying means other than the roller means. When automatically conveying the X-ray picture film 20, the conveying speed of the X-ray picture film 20 conveyed by the film conveying means 24a should be naturally regulated so as to match with the detecting speed of the light detecting means 23a. Of course, the X-ray picture film 20 may be conveyed in either a continuous manner or an intermittent manner.

The bone measurement apparatus according to the present invention is further provided with an image memory means 56 for storing the pictures of the X-ray picture film 20 arranged in the bone measurement data processing unit 32.

The image memory means 56 may be comprised of any type of means that is capable of storing either a first data including digital signals indicative of the intensity levels of light transmitting through the bone picture in the X-ray picture film 20 and respective positions of the X-ray picture film 20 in the conveying direction or a second data indicative of the pictures in the X-ray picture film 20 in the form of digital values obtained by converting the intensity of the transmitting light into corresponding thickness values of the aluminum step wedge 11 (FIG. 1). The size and capacity of the image memory means 56 should be selected depending on the purpose of the bone measurement or morphometry. For example, when the bone measurement of the second metacarpal bone (FIG. 1) is carried out, the image memory means 56 may be comprised of an IC image memory or a micro computer chip having approximately 2 megabyte.

The bone measurement apparatus according to the present invention is further provided with a micro processing unit arranged in the bone measurement data processing unit 32, which unit is capable of functioning as a judgement means for carrying out the afore-mentioned various judging operations as well as the illumination light adjustment operation in addition to the conventional functions such as an input function, memory function, and a calculating function.

As shown in FIG. 4, the data processing unit 32 interconnected with the automatic reading unit 31 is provided with a micro processing unit (MPU) 60 connected, via a bus line 58, to an image input/output means 55, the above-mentioned memory means 56, an interface (PIO) 57, a ROM 61, a RAM 62, a keyboard interface (KB I/F) 63 connected to a keyboard 51, a display controller CRTC 64 connected to a CRT 52, a printer interface PRI/F 65, connected to a printer 53, a RS-232 C 66 connected to a MODEM 54. The MPU 60 is capable of conducting, in cooperation with the ROM 61, a detection of a region of the picture of the standard matter, i.e., the aluminum step wedge, which region satisfies a predetermined condition regarding the quantity of light transmitting the picture of the standard matter, the afore-mentioned first and second judgement functions, and the afore-mentioned illuminating light adjustment function. The MPU 60 has a memory function therein for storing an operational condition such that an increase in the quantity of transmitting light transmitting through the aluminum step wedge 11 in response to an increase of the thickness by one step must have, after A/D conversion, a numerical value larger than 2 digits. The memory means of the MPU 60 must also store the values $I_1$, $I_2$, $S_1$, $S_2$, and other required values for enabling the MPU 60 to conduct the first judgement function.

In order to conduct the afore-mentioned second judgement function, the MPU 60 is also provided with an input and store function for inputting and storing a standard for an judgement regarding the afore-mentioned $\Delta I$.

Further, the MPU 60 capable of functioning as the illumination light adjustment means has a function to determine an adjusted quantity of illumination light and to operate the light adjusting operation of the LED controller during the bone measurement operation.

Furthermore, the MPU 60 needs to have an input/-memory function for inputting and storing the afore-mentioned values Imax and Imin, a calculating function to calculate the value $I_1'$, and a comparison function to make various comparing operations.

The afore-mentioned Table 1 is preliminarily stored in the ROM 61, thereby permitting the MPU 60 to effectively conduct the illumination adjustment operation.

The CRT 52 of the bone measurement apparatus of FIG. 4 is provided for displaying the picture of the sample bones in the X-ray picture film 20 as a display image, when sent from the image memory 56 or directly from the light detecting means 23a. The CRT 52 has a good image resolution from the view point of displaying cost. As required, the CRT 52 may, however, be replaced with another appropriate display means that is capable of displaying data including digital signals of the pictures of the X-ray picture film 20, obtained from the light detecting means 23a or from the image memory in relation to the position of the X-ray picture film 20 in the conveying direction.

The bone measurement apparatus of FIG. 4 must further be provided with an input means for inputting a reference point with regard to the displayed image of the sample bone in the X-ray picture film 20, which reference point is necessary for the bone measurement. The data processing of the bone measurement regarding the sample bone on the basis of the input reference point is carried out by the MPU 60. The above-mentioned reference point input means may be any one of a cursor control means, a light-pen input means, a touch-panel input means, and an automatic input means for inputting the reference point by automatically reading the stored bone picture from the image memory 56.

The bone measurement apparatus according to the present invention carries out the adjustment of the illumination light in the manner described below. Namely, when it is found that the adjustment of the illuminating light is required for obtaining accurate bone measurement data, the MPU 60 of the unit 32 permits the RAM 62 to store the position of the reference point that was input by the above-mentioned reference point input means on the displaying means, i.e., the CRT 52 before the illuminating light adjustment operation is started. The MPU 60 then conducts the afore-mentioned judgement operations to determine an amount of adjustment of the illuminating light. When the adjustment of the illuminating light applied to the X-ray picture film 20 is accomplished, the MPU 60 causes the light detecting means 23a to detect the quantity of light transmitting through the pictures of the X-ray picture film 20 with regard to the adjusted illuminating light, that is, the reading of the pictures of the X-ray picture film 20 is carried out. The image of the pictures of the X-ray picture film 20 is displayed on the display means, i.e., the CRT 52 on the basis of the above-mentioned reading to thereby permit the reference point input means to newly input the reference point with regard to the displayed image, on the basis of the reference point stored in the RAM 62.

It will be understood from the above-described operation that, in accordance with the bone measurement apparatus of the present invention when the intensity level of the illuminating light after adjustment is different from that of the illuminating light used at the preceding time, the X-ray picture film 20 is automatically conveyed to a position where the examined region of the picture of the sample bones and the picture of the aluminum step wedge are illuminated by the illuminating light after adjustment, and the reference point for the bone measurement is then automatically input on the basis of the reference point stored in the RAM 62. Thus, an operator of the apparatus is relieved of the burden of repeating a cumbersome data-input operation.

The printer 53 of the bone measurement data processing unit 32 may be comprised of, for example, a hard copying machine including a dot-type ink printer, a thermal printer, a laser printer, or a video printer. The printer 53 may also be comprised of a CRT displayer.

The printer 53 functions to output the bone measurement data.

The light emitting means 22a and the light detecting means 23a of the reading unit 31 may preferably be comprised of a band-like light source made of a plurality of light emitting diodes emitting a band-like light applied to an upper or rear surface of the X-ray picture film 20, and a line sensor made of a charge coupled device (CCD) including, e.g., 4,096 elements linearly arranged at a pitch of 65 microns across the X-ray picture film 20 in the direction perpendicular to the conveying direction of the film. Preferably, the light that has transmitted through the X-ray picture film 20 is focussed by a rod-like lens onto the light detecting means 23a, i.e., the line sensor which delivers a signal indicating quantity or intensity of transmitting light depending on the tone of the X-ray picture film 20. Namely, the line sensor of the light detecting means 23a delivers an electric analogue voltage in proportion to the incident quantity of light to the line sensor.

The film conveying means 24a of the reading unit 31 preferably includes a stepping motor capable of driving the conveyer rollers to thereby intermittently convey the X-ray picture film 20, such as at 65 microns pitch, in the direction perpendicular to the arranged direction of the line sensor.

The film feed controller 47 is provided for controlling the above-mentioned intermittent film conveying operation of the film conveying means 24a.

The CCD driver 46 controls the line sensor (CCD) of the light detecting means 23a so that the bone measuring data detected by the line sensor is delivered to the A/D converter 49 at a predetermined timing. The detected bone measuring data is further delivered from the A/D converter 49 to the image memory 56, via the image I/O means 55 so as to be stored therein. The stored bone measuring data can be displayed on the CRT 52, via the CRT controller (CRTC) 64.

The CRT 52 that is preferably a 7 inch CRT (640 dots×400 lines) displays e.g., an image of the metacarpal bone, and a portion of the image to be examined, for example, bone head and end, is designated by the pointing device means made of the keyboard 51 and the key board interface (KB I/F) 63.

The calculating operation for the bone measurement on the basis of the data read by by the reading unit 31 is carried out mainly by the MPU 60 of the unit 32 in accordance with the operation program stored in the ROM 61, and the calculation result including various measured data of the sample bone is erasably stored in the RAM 62. The measuring data is delivered as visible data by the output means including the printer interface (PRI/F) 65 and the printer 53, and can be also sent to various kinds of external apparatus by a communication line I/F means including the RS-232C I/F 66 and the modem 54.

The MPU 60 is preferably constituted by a conventional 16 bit microprocessor, and has a function of controlling the data reading-in operation of the image memory 56, an initial start and stop of the operational program, and the operation of the key board 51 and the CRT 52, in addition to the aforementioned various calculating operation necessary for the adjustment of the illuminating light and the bone measurement, From the foregoing description of the preferred embodiments of the present invention, it will be understand that in accordance with the bone measurement method of the present invention, an adjustment of light illuminating an X-ray picture film having pictures of the sample bones and the standard matter is automatically and effectively achieved, thereby enabling the measurement of the bone data irrespective of the tone condition of the pictures in the X-ray picture film. Further, in accordance with the bone measurement apparatus for the present invention, an effective and simple means for adjusting the illuminating light applied to an X-ray film having the pictures of sample bones and the standard matter in response to a difference in the tone of the pictures, to thereby ensure an accurate detection and measurement of the data of the sample bone via the X-ray picture film.

Figure 9:
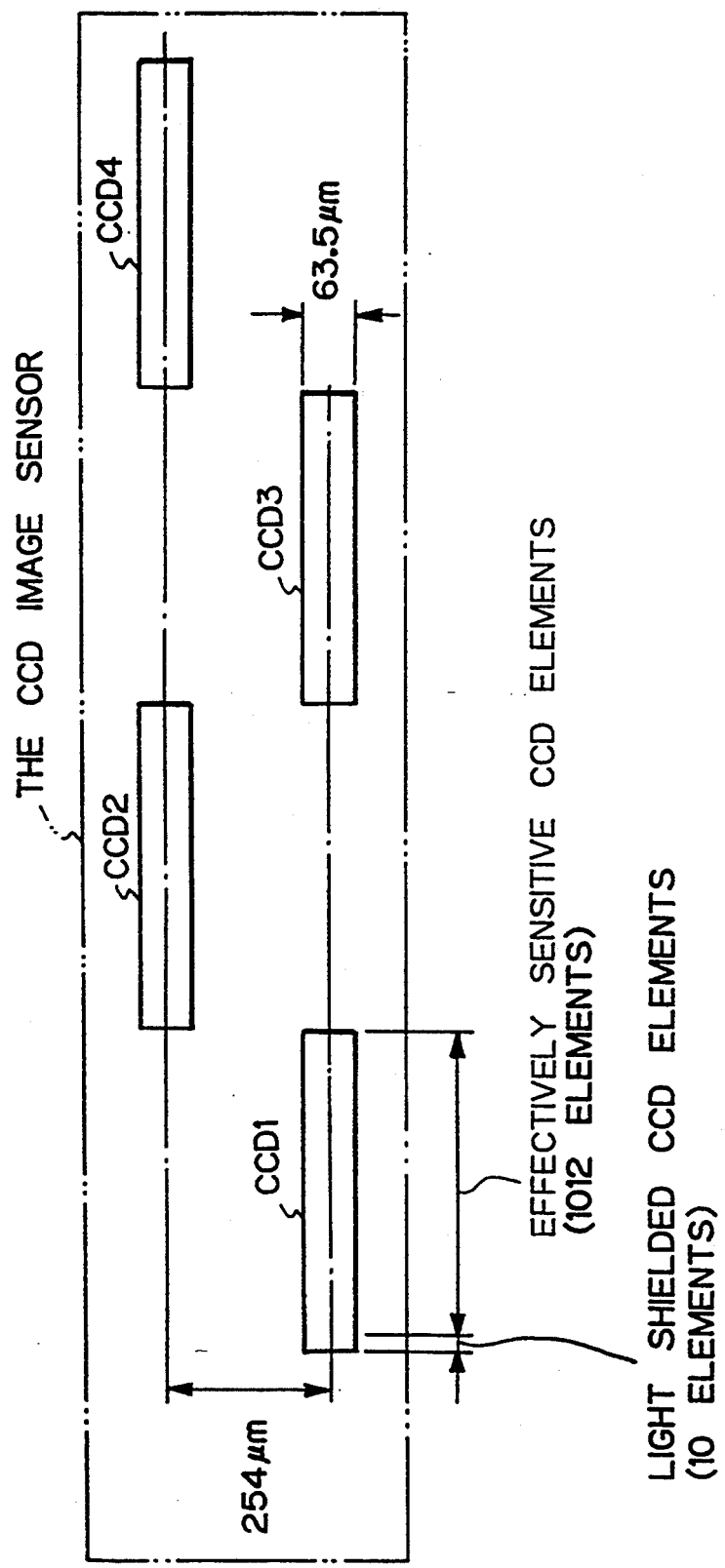
FIG. 9 is a schematic view illustrating an example of the CCD image sensor constructed by four CCD chips having 1,012 CCD elements and 10 light shielding elements.

FIG. 9 illustrates an example of the internal arrangement of the line sensor, i.e., the CCD image sensor capable of being used with, for example, the bone measurement apparatus according to the present invention, as shown in FIG. 4.

Figure 8:
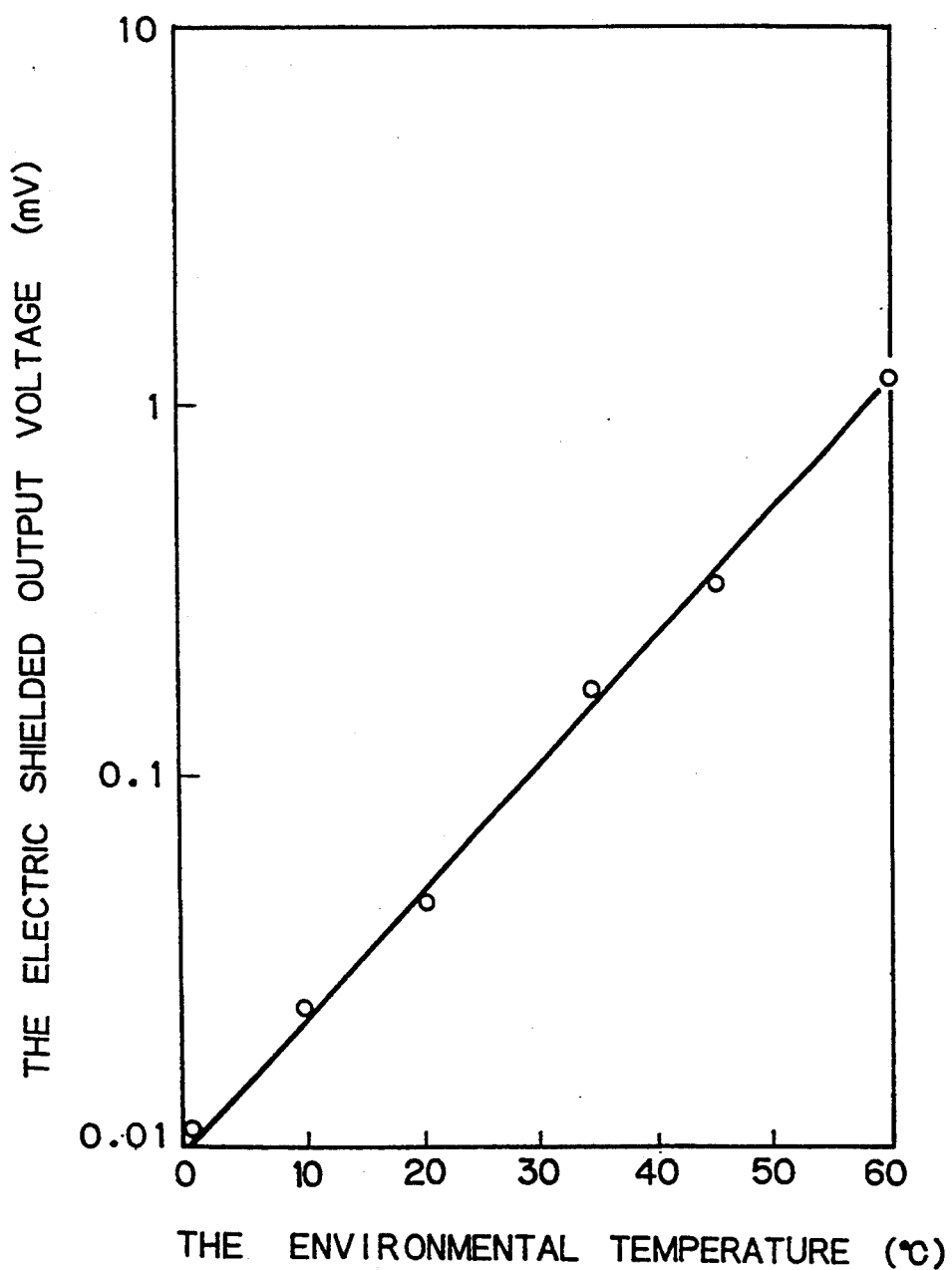
FIG. 8 is a graph generally illustrating a relationship between the electric shielded output voltage of the charge coupled device (CCD) image sensor and the environmental temperature around the CCD image sensor.

In FIG. 9, the CCD image sensor is constructed as an assembly of four CCD chips CCD1 through CCD4, and each of the four chips CCD1 through CCD4 has 1,012 effectively sensitive CCD elements, and 10 light shielding CCD elements. The effectively sensitive CCD elements of each chip of the CCD image sensor function to detect an intensity or quality of light applied to respective elements and to deliver a corresponding electric output voltage at the output thereof, and the light shielded CCD elements of each chip function to deliver an electric output voltage when no light is applied to these elements. Namely, the light shielded CCD elements of each chip CCD1, CCD2, CCD3 or CCD4 indicate the electric shielded output voltage of each CCD chip. Since the electric shielded output voltage of each chip changes in response to an increase in the environment temperature of the CCD image sensor as shown in FIG. 8, and since the electric detected output voltage of the effectively sensitive CCD elements of each chip contains therein the electric shielded output voltage component, an appropriate means for compensating for the thermal change of the electric shielded output voltage of each chip of the CCD image sensor must be provided for improving the detecting and measuring accuracy of the CCD image sensor.

In accordance with the present invention, there is provided a novel temperature compensating means for enhancing the detecting and measuring accuracy of the CCD image sensor used with the bone measurement of FIG. 4.

Briefly, the principle of the novel temperature compensation achieved by the temperature compensating means of the present invention is characterized in that a first order compensation for the electric shielded output voltage of the CCD image sensor is cursorily carried out by utilizing the electric shielded output voltage delivered by the CCD image sensor per se, and that a second order compensation including the steps of measuring a remaining electric shielded output voltage after the first cursory compensation, with a state such that the CCD image sensor is shielded from light, and subtracting the measured remaining electric shielded output voltage from the electric output voltage of the CCD image sensor exposed to light is carried out to achieve an accurate temperature compensation of the output signals of the CCD image sensor.

The operation of the temperature compensation of the CCD image sensor according to the present invention will be described more in detail with reference to FIGS. 10 through 12B.

In accordance with the present invention, when the image sensor 23a, essentially comprised of a plurality of CCD chips having a plurality of CCD elements, respectively, is used for detecting light that transmits through or is reflected from a photographic or radiographic picture film containing therein pictures, measurement of a part of light-shielded electric output voltages $V_0$ (I) with regard to at least one selected chip of the CCD image sensor is initially carried out. At this stage, it should be understood that the above-mentioned at least one of the plurality of chips technically indicates one or more chips of the CCD image sensor that has actually functioned to detect the transmitting light of the picture film.

Subsequently, regarding each CCD element (X) of the selected chip, measurement of electric output voltages V (X) at the time of exposure to light is carried out, to thereby obtain a first order compensation electric voltage V1 (X) corresponding to $V(X) - V_0(I)$. Then, with regard to each of the CCD elements of the selected chip, measurement of first order light-shielded electric output voltages $V1_0$ (X) is carried out by applying no light to each CCD element, and the measured first order light-shielded electric output voltages $V1_0$ (X) are subjected to A/D conversion by the A/D converter 49 to obtain $NV1_0(X)$. Further, with regard to each CCD element of the selected chip of the CCD image sensor, the above-mentioned first order compensation electric voltage V1 (X) is subjected to A/D conversion by the A/D converter 49' to obtain the corresponding digital value NV1 (X), and subtracting calculation of an equation defined as $NV1(X) - NV1_0(X)$ is further carried out by the MPU 60' to obtain a second order compensated electric output value NV2 (X).

The obtained electric output value NV2 (X) is used as data on which further processing is carried out by a data processing unit such as the bone measurement data processing unit 32 of FIG. 4, to thereby obtain various information of the picture in the photographic or radiographic picture film. Of course, the above-mentioned method can be applied to detection and measurement of only a part of the picture in the film, e.g., a part of the picture of the sample bones of the X-ray picture film 20 (FIG. 4).

Furthermore, in accordance with the present invention, in addition to obtaining of the above-mentioned A/D converted values of $NV1_0$ (X) and NV1 (X), it is possible to obtain a shading value NR1 (X) after A/D conversion by the operation of the MPU 60, to thereby obtain a second order compensated electric output value NVS (X) that is simultaneously subjected to the shading compensation, through a calculation of the equation below.

$$NVS(X) = K_1[NV1(X) - NV1_0(X)]/[NR1(X) - NV1_0(X)] \quad (2)$$

where $K_1$ is a predetermined constant.

Furthermore, after obtaining of the above-mentioned second order compensated electric output value NV2 (X), a shading value NR2 (X) after the second order compensation and the A/D conversion is found to thereby obtain a second order compensated value NVS (X) that is simultaneously subjected to the shading compensation, through the calculation of the equation (3), below.

$$NVS(X) = K_2[NV2(X)]/[NR2(X)] \quad (3)$$

where $K_2$ is a predetermined constant.

The above-mentioned electric shielded output voltage $V_0$ (I) may be the minimum value in the electric shielded output voltages of the CCD elements of the selected chip of the CCD image sensor.

In order to perform the above-described compensation method, there is provided a temperature compensating unit capable of providing a CCD image sensor essentially comprised of a plurality of CCD chips including a plurality of CCD elements, respectively, with a temperature compensation when the CCD image sensor is used for detecting a light emitted from a light source means and transmitting through or being reflected from a measured picture in a photographic or radiographic picture film. The temperature compensating unit includes: a first order measurement controlling means for measuring a part of the electric shielded output voltages $V_0$ (I) with regard to at least one selected chip of the CCD image sensor, and an electric output voltage V (X) at the time of exposure to light with regard to each CCD element (X) of the selected chip of the CCD image sensor;

a first order compensation means for calculating a first order compensation electric voltage V1 (X) corresponding to the value of $[V(X) - V_0(I)]$ for compensating for the electric shielded output voltage of the CCD image sensor;

an A/D converter means for making an A/D conversion of the first order compensation electric voltage V1 (X);

a second order measurement controlling means for measuring a first order electric shielded output values $NV1_0(X)$ that is obtained by shielding the CCD elements of the selected chip after A/D conversion of the first order compensation electric voltage, and a first order output value NV1 (X) at the time of exposure to light, which value is obtained by subjecting the first order compensation electric voltage V1 (X) to an A/D convertion; and a second order compensating means for calculating a second order compensated output value NV2 (X) in the form of a numerical value, as a result of the calculation of an equation defined as $NV2(X) = NV1(X) - NV1_0(X)$.

The above-mentioned light source means is preferably comprised of a band-like LED light source having a plurality of linearly arranged LED elements. As required, the light source means may also be comprised of a plurality of optical fibers arranged in a manner such that one end of each optical fiber is linearly disposed in a plane, and the other end is used as light input end.

The CCD image sensor may either be a CCD line sensor including a plurality of CCD chips, as shown in FIG. 9 or a CCD area sensor (not shown).

Figure 10:
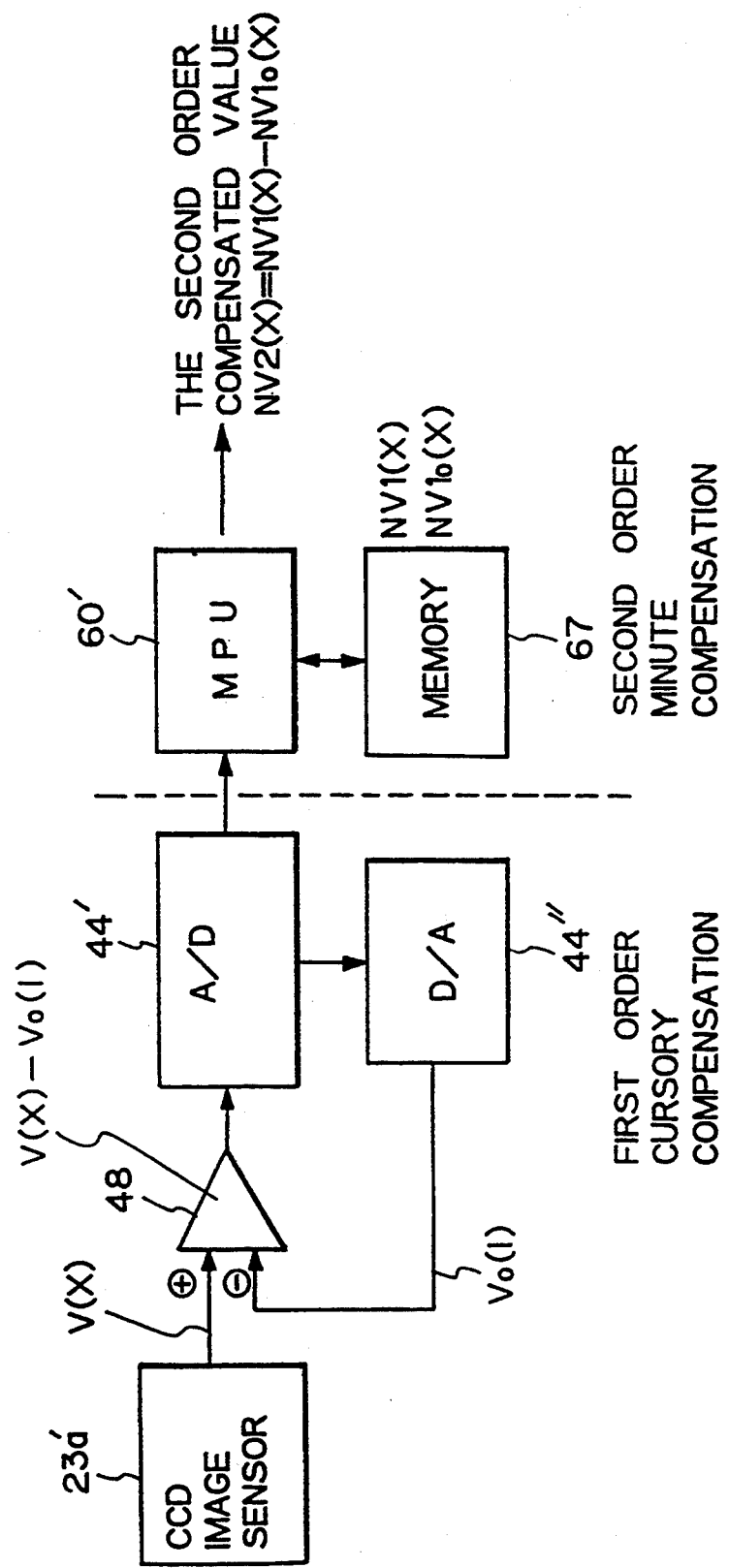
FIG. 10 is a schematic block diagram illustrating the temperature compensation unit for the electric output voltage of the CCD sensor of FIG. 9.

A typical arrangement of the above-mentioned temperature compensating unit is shown in FIG. 10.

As shown in FIG. 10, the temperature compensating unit is constructed so as to apply a temperature compensation to the output data of a CCD image sensor 23a', and includes an operation Amplifier 48, an A/D converter 44', a D/A converter 44", an MPU (microprocessor unit) 60' and a memory means 67.

Figure 11:
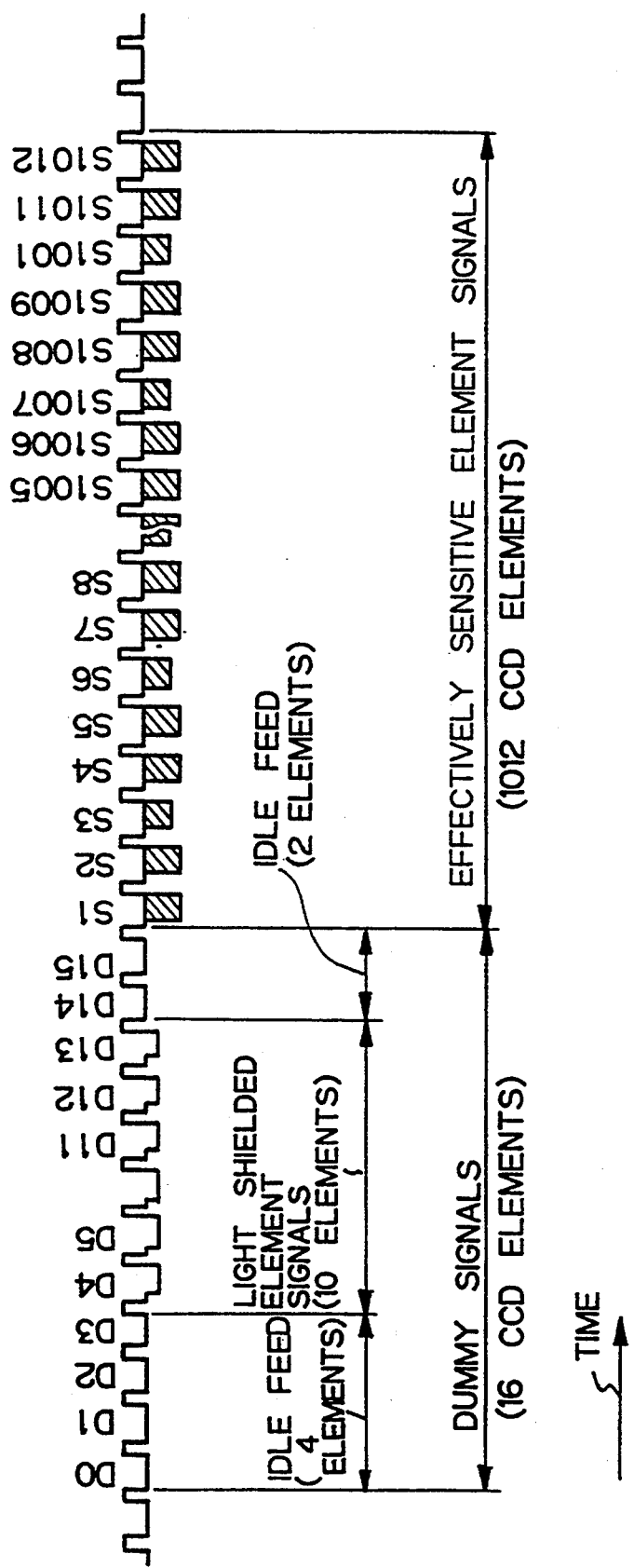
FIG. 11 is a graphical view of a CCD image sensor provided with the light shielding elements therein, and illustrating a time chart of the output derived from the CCD image sensor.

The temperature compensating unit of FIG. 10 is able to function as the afore-mentioned first measuring controlling means to measure the electric shielded output voltages $V_0$ (I) from at least one selected chip of the CCD image sensor 23a', and an electric output voltage V (X) at the time of exposure to light with regard to each CCD element of the selected chip of the CCD image sensor 23a' in accordance with a timing as shown in the time chart of FIG. 11.

The unit of FIG. 10 is also able to function as the afore-mentioned first order compensation means for calculating a first order compensation electric voltage V1 (X) corresponding to the value $(V(X)-V_0(I))$ for compensating for the light-shielded electric output voltage of the CCD image sensor 23a'. Thus, the unit of FIG. 10 functions to apply an A/D conversion to the light-shielded output voltage $V_0$ (I) from the selected one of the CCD chips of the CCD image sensor 23a', and to hold the A/D converted shielded output voltages $NV_0(I)$ for a time period during which the selected one of the chips of the CCD image sensor 23a' delivers the electric output voltages V (X) at the time of exposure to light. The unit further functions to apply a D/A conversion to the held A/D converted shielded output voltage $NV_0(I)$ to return the $NV_0(I)$ to the value $V_0(I)$, and compensates for the electric output voltages V (X) to obtain the compensated output voltage $V_1$ (X) by calculating an equation defined by $V_1(X) = V(X) - V_0(I)$.

Since respective CCD chips of the CCD image sensor 23a' have individual thermal properties different from one another, and respective thermal properties gradually change due to the time lapse. Therefore, the above-mentioned first order compensation operation carried out by the first order compensation means of the unit of FIG. 10 should be implemented with respect to each of the CCD chips of the CCD image sensor 23a', that is actually used for the measurement of the picture in the film. Also, the first order compensation operation should be renewed at each time the selected chip or chips are scanned.

Since each chip of the CCD image sensor 23a' is provided with a plurality of (approximately 10) light shielded CCD elements, as shown in FIG. 9, the above-mentioned electric shielded output voltage $V_0$ (I) used for a cursory temperature compensation may be either any one of the electric shielded voltages delivered from the plurality of light shielded CCD elements or a voltage value obtained by averaging all of the electric shielded output voltages delivered from the plurality of light shielded CCD elements. However, the former one should preferably be employed from the view point of simplifying the entire arrangement of the temperature compensating unit and from the viewpoint of the reduction of the manufacturing cost of the unit. In this connection, the electric shielded output voltage $V_0$ (I) used for cursory temperature compensation should preferably be the smallest one of the electric shielded voltage delivered from the plurality of light shielded CCD elements from the viewpoint of avoiding an excessive compensation in the cursory temperature compensation step.

The electric shielded output voltage $V_0$ (I) in the form of an analogue signal, is usually very small, and therefore should be subjected to an A/D conversion after it is amplified into a larger voltage signal, e.g., a voltage signal being 10 through 20 times amplified, to thereby obtain an accurate A/D converted digital signal. When the A/D converted digital signal is returned to the original analogue signal by the D/A converter 44", the signal should be suitably divided to the original low value.

The temperature compensating unit of FIG. 10 is also able to function as the above-mentioned second order measuring and controlling means. Namely, the second order measuring and controlling means may be a combination of the MPU 60' capable of controlling the LED light source, via a LED controller (not shown in FIG. 10), and a random access memory (RAM) and a read only memory (ROM) which form the memory 67. The LED controller controlled by the MPU 60' in turn controls the LED light source in a manner such that when the electric shielded output voltage $V1_0$ (X) of each of the CCD elements is measured, the illuminating level of the LED light source is turned off, to substantially zero illumination level, and that when the electric output voltage V1 (X) of each of the CCD elements is measured, the illumination level of the LED light source is set at a predetermined illumination level. The RAM of the memory 67 stores all data during the temperature compensating operation, and the ROM of the memory 67 stores the control program implemented by the MPU 60' during the temperature compensating operation.

The unit of FIG. 10 is further able to function as the afore-mentioned second compensating means. The second compensating means may be comprised of: the RAM of the memory 67 which stores the value $NV1_0$ (X) corresponding to an A/D converted value of the first electric shielded voltage value $V1_0$ (X), and NV (X) corresponding to an A/D converted value of the first electric output voltage V1 (X) at the time of exposure to light; the MPU 60' which obtains the second compensated output value N2 (X) by calculating the equation defined as $N2(X) = NV1_0(X) - NV_1(X)$; and the ROM of the memory 60' which stores the calculating program.

The MPU 60' may be used for applying a shading compensation to the LED light source, the CCD image sensor 23a', and a rod-like lens used for focussing the transmitting light that has transmitted through the objected picture film. The shading compensation is carried out for compensating for differences in the photo-electric property of elements of the LED light source, the CCD image sensor 23a', and the rod-like lens, either in parallel with or after the completion of the above-mentioned second order temperature compensating operation. For example, with regard to each CCD element (X) of each of the chips of the CCD image sensor 23a', a first order electric shielded output voltage is measured under the application of zero level of light to the CCD image sensor, and subsequently, an electric shading voltage after the first order compensation is measured under the application of a predetermined level of light to the CCD image sensor. Further, the electric output voltage of the CCD image sensor during the measurement of the picture in the picture film is measured. All of the measured data are stored in the RAM of the memory 67. Then, the temperature compensation and the shading compensation are simultaneously carried out by calculating the afore-mentioned equation (2).

Furthermore, with regard to each CCD element of each of the chips of the CCD image sensor, a shading output after the second order compensation of the electric shielded output voltage is measured under the application of a predetermined level of light to the element, and also the electric output voltage of the CCD element during the measurement of the picture in the film is measured. Subsequently, the compensation on the afore-mentioned equation (3) is carried out.

Figure 12A:
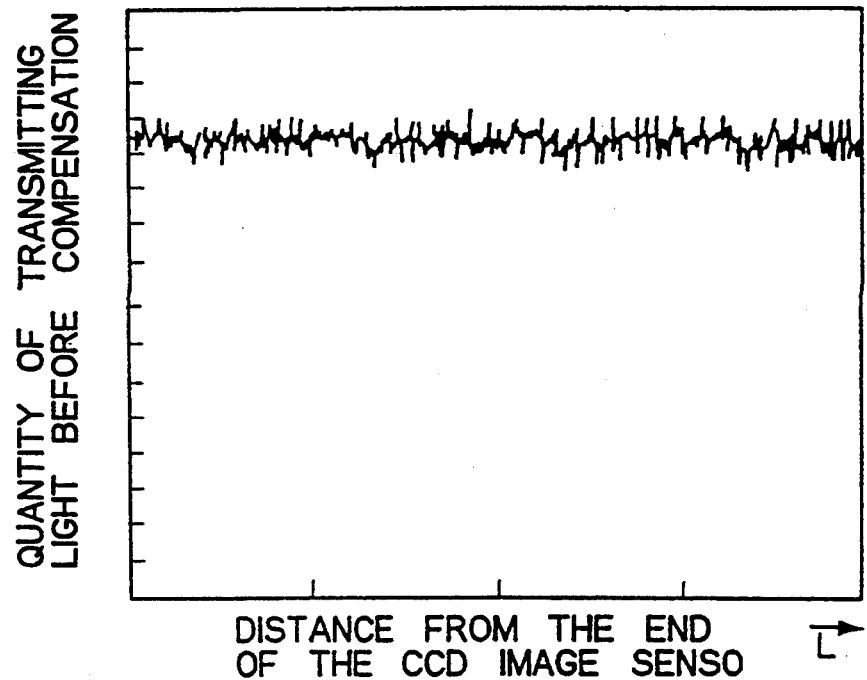
FIGS. 12A and 12B are graphs illustrating the effect of compensation when employing the shading compensation.

FIG. 12A indicates the relationship between the linear position of the CCD image sensor and the quantity of light transmitting an objective film before the shading compensation.

Figure 12B:
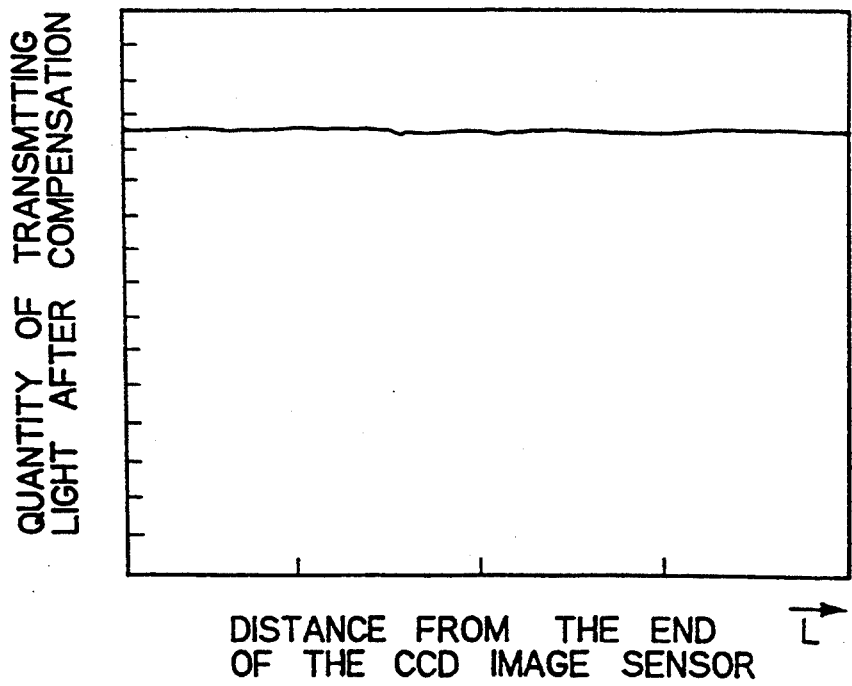

FIG. 12B indicates the relationship between the linear position of the CCD image sensor and the quantity of light transmitting an objective film after the shading compensation.

Figure 13:
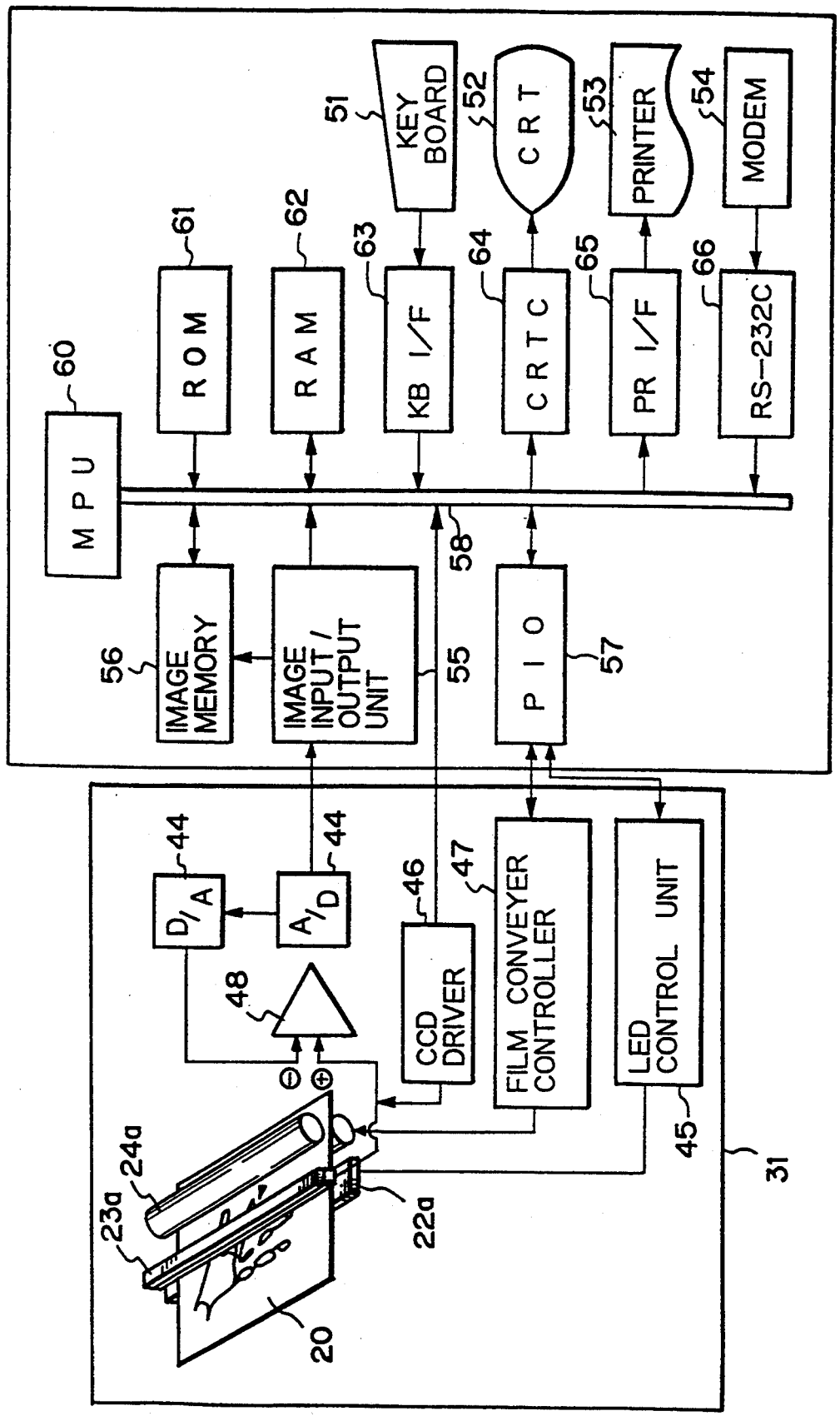
FIG. 13 is a block diagram illustrating a bone measurement apparatus in which the temperature compensation unit of the present invention is incorporated.

FIG. 13 illustrate the entire arrangement of a bone measurement apparatus in which the afore-described temperature compensation unit is incorporated. Namely, when the bone measurement apparatus of FIG. 13 is employed for measuring bone data of an X-ray picture film, the measured data detected by the CCD image sensor $23a'$ and thermally compensated for by the temperature compensation unit can be accurate more than those obtained by the apparatus of FIG. 4 due to reduction of thermal drifting of the data. When the bone measurement apparatus of FIG. 13 is used for calculating bone data of a human second metacarpal bone from the data obtained from the CCD image sensor $23a'$ with regard to the radiographical picture of the second metacarpal bone in an X-ray picture film, it is possible to obtain data similar to the data shown in FIG. 3. Nevertheless, as shown in FIG. 14 illustrating a relationship between the temperature and the bone density data $\Sigma$ GS/D, the data can be more accurate due to either the first order temperature compensation or the first and second order temperature compensation, compared with no temperature compensation.

From the foregoing description of the diverse embodiments of the present invention, it will be understood that the accuracy of the bone measurement or bone morphometry can be greatly improved.

We claim:

1. A method of measuring bone, in which a light is illuminated onto an X-ray film having therein both of simultaneously taken radiographic pictures of sample bones to be examined and of a given standard matter having a gradational thickness to detect a light transmitting through the pictures of the X-ray picture film, thereby using a detected quantity of the transmitting light for a measurement of a sample bone data, wherein said method comprises the steps of:

selecting a given quantity Lc of light illuminating said pictures in the X-ray picture film, from a preset plurality of quantities of illuminating light;

applying said selected quantity Lc of illuminating light to the X-ray picture film for illuminating said pictures thereby allowing a cursory reading of said pictures in the X-ray picture film to obtain a cursory information of pixel of said pictures through detection of quantity of transmitting light that transmits through various regions of said pictures in the X-ray picture film;

determining a maximum quantity ICmax of transmitting light from detected quantities of transmitting light transmitting through a predetermined examined region of a picture of the sample bones during said cursory reading of the pictures in the X-ray picture film;

applying a predetermined quantity $L_1$, of illuminating light to the X-ray picture film for illuminating said picture thereof and for allowing a detailed reading of a picture of the given standard matter through detection of transmitting light that transmits through the picture of said given standard matter;

detecting a thickness $R_1$ of the standard matter which permits the illuminating light to transmit therethrough, a quantity of said transmitting light being close to and more than said maximum quantity level ICmax of light;

determining a quantity $I_{R1}$ of transmitting light that transmits through the picture of the standard matter at a portion thereof having a thickness $R_1$; and adjustably changing a quantity of illuminating light for illuminating the X-ray picture film until an obtained quantity $I_{R1}$ of transmitting light is close to a predetermined quantity Imax of transmitting light without exceeding said predetermined quantity Imax of transmitting light.

2. A bone measuring method according to claim 1, wherein said method further comprises the steps of:

detecting a portion of the picture of the standard matter, in which portion a quantity of transmitting light that transmits through said portion satisfies a predetermined condition;

conducting a first judgement as to whether or not said quantity of transmitting light that transmits through a predetermined examined region of the X-ray picture film of the sample bones exists in quantity range of transmitting light that transmits through the detected portion of said picture of the standard matter;

conducting a second judgement as to whether or not the quantity of transmitting light that transmits through said picture of the standard matter corresponding to quantity of transmitting light that transmit through said predetermined examined region of the picture of a sample bone is able to exhibit a resolving power satisfying a predetermined resolution; and further adjustably changing a quantity of illuminating light for illuminating said X-ray picture film on the basis of said second judgement.

3. A bone measuring method according to claim 2, wherein said method is further characterized by additionally including the steps of:

conducting a third judgement as to whether or not a gradient value $\gamma$ in said predetermined examined region of the picture of the sample bone is equal to or larger than a predetermined gradient value regarding the X-ray picture film.

4. An apparatus for measuring bone data by using an X-ray picture film having therein a radiographic picture of sample bones and a simultaneously taken picture of a given standard matter having a gradational thickness, comprising in combination:

a reading means for reading the pictures by using a quantity of light that transmits through said pictures of the X-ray picture film illuminated by a given quantity of light, said reading means comprising a light emitting means for emitting said given quantity of light illuminating said X-ray picture film, and a light detecting means for detecting a quantity of light that transmits through the X-ray picture film;

a storing means for storing said picture of said sample bones read by said reading means;

an operating means for calculating bone data of said picture of said sample bones stored in said storing means;

an output means for delivering said bone data calculated by said operation means as bone-data output, means for selecting a given quantity Lc of illuminating light for illuminating the pictures in the X-ray picture film, from a preset plurality of quantities of illuminating light;

means for applying the selected quantity Lc of illuminating light to the X-ray picture film for illuminating said pictures therein, and for permitting said light detecting means to implement a cursory reading of said pictures in the X-ray picture film for obtaining a cursory information of pixel of said pictures through detection of quantity of transmitting light that transmits through various regions of said pictures in the X-ray picture film;

means for determining a maximum quantity ICmax of transmitting light from the detected quantities of light transmitting through a predetermined examined region of said picture of the sample bones during said cursory reading of the pictures in the X-ray picture film, said predetermined quantity $L_1$ of illuminating light being applied to the X-ray picture film for illuminating said pictures thereof thereby permitting said reading means to implement a detailed reading of the picture of the given standard matter in the film through detection of light transmitting through the picture of said given standard matter;

means for detecting a thickness portion $R_1$ of the picture of the standard matter which permits the illuminating light to transmit therethrough, a quantity of said transmitting light that transmits through said thickness portion of the standard matter being close to and more than said maximum quantity ICmax of light;

means for determining a quantity $I_{R1}$ of light that transmits through the picture of the standard matter at a portion thereof having a thickness $R_1$;

a first light adjusting means for adjustably changing a quantity of illuminating light emitted by said light emitting means and illuminating the X-ray picture film until the obtained quantity $I_{R1}$, of transmitting light is close to a predetermined quantity Imax of transmitting light without exceeding said predetermined quantity Imax of transmitting light;

a region detecting means for detecting a portion of the picture of the standard matter, in which portion a quantity of transmitting light that transmits through said portion satisfies a predetermined condition;

a first judgement means for conducting a first judgement as to whether or not said quantity of transmitting light that transmits through a predetermined examined region of the X-ray picture film of the sample bones exists in quantity range of transmitting light that transmits through the detected portion of said picture of the standard matter;

a second judgement means for conducting a second judgement as to whether or not the quantity of transmitting light that transmits through said picture of the standard matter corresponding to the quantity of transmitting light that transmit through said predetermined examined region of the picture of the sample bones is able to exhibit a resolving power satisfying a predetermined resolution; and a second light adjusting means for further adjustably changing a quantity of illuminating light emitted by said light emitting means and illuminating said X-ray picture film on the basis of said second judgement.

5. A bone data measuring apparatus according to claim 4, further comprising:

means for conducting a judgement as to whether or not a gradient value $\gamma$ in said predetermined examined region of the picture of the sample bones is equal to or larger than a predetermined gradient value regarding the X-ray picture film.

6. A bone data measuring apparatus according to claim 4, further comprising:

an image display means for displaying the picture of the sample bone read by said reading means;

a point input means for inputting a reference point with regard to which said reading of the picture of the sample bones is carried out;

a reference point storing means for storing said reference point input by said point input means; and an automatic conveying means for providing the X-ray picture film with an automatic feed when the X-ray picture film is re-measured after adjustment of the quantity of illuminating light, to thereby permit said reading means to read the pictures of the sample bone and the standard matter, illuminated by the adjusted quantity of illuminating light; and means for inputting a new reference point regarding the picture of the sample bone on the basis of the stored reference point in said reference point storing means.

7. A bone data measuring apparatus according to claim 4, wherein said standard matter having the gradational thickness comprises an aluminum step wedge provided with a plurality of equally gradational steps.

8. A bone data measuring apparatus according to claim 4, wherein said light detecting means of said reading means comprises a CCD image sensor having an assembly of a plurality of CCD chips, each chip having at least a plurality of light shielded CCD elements and a plurality of effectively sensitive CCD elements, and wherein said apparatus further comprises a temperature compensating means for compensating for a detection output of said CCD image sensor, said temperature compensating means comprising:

a first order measurement controlling means for measuring a part of electric shielded output voltages $V_0$ (I) regarding at least one selected chip of said CCD image sensor, and an electric output voltage V (X) at the time of exposure to light with regard to each of said CCD element (X) of said selected chip of said CCD image sensor;

a first order compensation means for calculating a first order compensation electric voltage V1 (X) corresponding to the value of $(V (X) - V_0 (I))$ for compensating for the electric shielded output voltage of said CCD image sensor;

an A/D converter means for making an A/D conversion of the first order compensation electric voltage V1 (X);

a second order measurement controlling means for measuring a first order electric shielded output value NV1$_0$(X) that is obtained by shielding said CCD elements of said selected chip after A/D conversion of said first order compensation electric voltage, and a first order output value NV1 (X) at the time of exposure to light, which value is obtained by subjecting said first order compensation electric voltage V1 (X) to an A/D conversion; and a second order compensating means for calculating a second order compensated electric output value NV2 (X) as a result of the calculating of an equation defined as NV2 (X)=NV1 (X)−NV1$_0$ (X).

9. A bone data measuring apparatus according to claim 8, wherein said light emitting means comprises a band-like LED light source means arranged above or below a surface of said X-ray picture film.

10. A method of measuring bone including illuminating an X-ray picture film having therein both of simultaneously taken radiographic pictures of sample bones and a given standard matter having a gradational thickness by a light emitted by a light emitting means, and detecting a light transmitting through the pictures of the X-ray picture film by a CCD image sensor having an assembly of a plurality of CCD chips, each chip having at least a plurality of light shielded CCD elements and a plurality of effectively sensible CCD elements, wherein the method comprises the steps of:

measuring a part of electric shielded output voltages V$_0$ (I) with regard to at least one selected chip of the CCD image sensor;

measuring electric output voltages V (X) at the time of exposure to light, with regard to each CCD element (X) of the selected chip, to thereby obtain a first order compensation electric voltage V1 (X) corresponding to V (X)−V$_0$ (I);

measuring first order compensation electric shielded output voltages V1$_0$ (X) with regard to each of said CCD elements of said selected chip, under a condition that each of said CCD elements is shielded from light; and applying an A/D conversion to the measured first order compensation electric shielded output voltages V1$_0$ (X) to thereby obtain NV1$_0$(X);

detecting first order compensation electric shielded voltage V1 (X), with regard to each of said CCD elements of said selected chip;

applying A/D conversion to said first order compensation electric shielded voltage V1 (X) to obtain a corresponding digital value NV1 (X); and implementing a subtractive calculation of an equation defined as NV1 (X)−NV1$_0$(X) to obtain a second order compensation electric output value NV2 (X), said obtained electric output value NV2 (X) being used as data on which further processing is conducted to read the pictures of the X-ray picture film.

11. A bone measuring method according to claim 10, wherein said second order compensation electric output value NV2 (X) is obtained with regard to only a part of the pictures in the X-ray picture film.

12. A bone measuring method according to claim 10, wherein the method comprises, in addition to obtaining of said A/D converted values of NV1$_0$ (X) and NV1 (X), obtain a shading value NR1 (X) to thereby obtaining a second order compensation electric output value NVS (X) that is simultaneously subjected to the shading compensation, through calculation of an equation below, $$NVS\ (X) = K_1\ [NV1\ (X) - NV1_0\ (X)] / [NR1\ (X) - NV1_0\ (X)],$$

where $K_1$ is a predetermined constant.

13. A bone measuring method according to claim 10, wherein the method further comprises, after obtaining said second order compensation electric output value NV2 (X), determining a shading value NR2 (X) after said second order compensation and the A/D conversion, to thereby calculate a second order shading compensated value NVS (X) after the second order compensation in accordance with an equation below, $$NVS\ (X) = K2\ [NV2\ (X)] / [NR2\ (X)],$$

where K2 is a predetermined constant.

14. A bone measuring method according to claim 10, wherein said part of electric shielded output voltages V$_0$ (I) with regard to at least one selected chip of the CCD image sensor comprises the smallest one of said electric shielded output voltages V$_0$ (I) obtained with regard to said CCD elements of said selected chip of said CCD image sensor.

* * * * *